US 8,975,058 B2

United States Patent
Leinonen et al.

(10) Patent No.: US 8,975,058 B2
(45) Date of Patent: Mar. 10, 2015

(54) ENDOGLUCANASES FOR TREATMENT OF CELLULOSIC MATERIAL

(71) Applicant: Roal Oy, Rajamäki (FI)

(72) Inventors: Taija Leinonen, Riihimäki (FI);
Alexandra Komander, Darmstadt (DE);
Kim Langfelder, Darmstadt (DE); Jari Vehmaanperä, Klaukkala (FI); Terhi Puranen, Nurmijärvi (FI)

(73) Assignee: Roal Oy (FI)

( * ) Notice: Subject to any disclaimer, the term of this patent is extended or adjusted under 35 U.S.C. 154(b) by 0 days.

(21) Appl. No.: 13/902,018

(22) Filed: May 24, 2013

(65) Prior Publication Data

US 2014/0051128 A1    Feb. 20, 2014

Related U.S. Application Data

(60) Provisional application No. 61/651,256, filed on May 24, 2012.

(51) Int. Cl.
*C12N 9/42* (2006.01)
*C12P 19/14* (2006.01)
*C12R 1/19* (2006.01)
*C12P 19/02* (2006.01)

(52) U.S. Cl.
CPC ............... *C12N 9/2437* (2013.01); *C12P 19/14* (2013.01); *C12N 9/244* (2013.01); *C12R 1/19* (2013.01); *C12P 19/02* (2013.01)
USPC ............ 435/209; 435/200; 435/99; 435/100; 435/101

(58) Field of Classification Search
None
See application file for complete search history.

(56) References Cited

U.S. PATENT DOCUMENTS

2007/0148732 A1*  6/2007  Valtakari et al. ............. 435/69.1

FOREIGN PATENT DOCUMENTS

| EP | 2374877 A2 | 10/2011 |
|----|----|----|
| WO | 9714804 | 4/1997 |
| WO | 0160752 A1 | 8/2001 |
| WO | 01/70998 A1 | 9/2001 |
| WO | 0224882 A3 | 3/2002 |
| WO | 2004078919 A3 | 9/2004 |
| WO | WO 2006074435 A2 * | 7/2006 |
| WO | 2007/071818 A1 | 6/2007 |

(Continued)

OTHER PUBLICATIONS

Vlasenko et al., "Substrate specificity of family 5, 6, 7, 9, 12, and 45 endoglucanases", Bioresource Technology, vol. 101, pp. 2405-2411, 2010.*

(Continued)

*Primary Examiner* — Rebecca Prouty
*Assistant Examiner* — Richard Ekstrom
(74) *Attorney, Agent, or Firm* — Banner & Witcoff, Ltd.

(57) ABSTRACT

The present invention relates to production of fermentable sugars from lignocellulosic material by enzymatic conversion. The fermentable sugars are useful e.g. in the production of bioethanol. Novel polypeptides having endoglucanase activity, polynucleotides encoding them and vectors and host cells containing the polynucleotides are disclosed. A method for treating cellulosic material with the novel endoglucanase as well as uses of the enzymes and enzyme preparations and a method of preparing them are described.

11 Claims, 5 Drawing Sheets

Expression cassette figure

(56) References Cited

FOREIGN PATENT DOCUMENTS

| | | | |
|---|---|---|---|
| WO | 2007/118935 | A1 | 10/2007 |
| WO | 2007115201 | A2 | 10/2007 |
| WO | WO 2009085859 | A2 * | 7/2009 |
| WO | 2011057140 | A1 | 5/2011 |
| WO | 2011080317 | A3 | 7/2011 |
| WO | 2011153516 | A2 | 12/2011 |
| WO | 2012062220 | A1 | 5/2012 |

OTHER PUBLICATIONS

Guo et al., "Protein tolerance to random amino acid change", Proceedings of the National Academy of Sciences USA, vol. 101, No. 25, pp. 9205-9210, 2004.*

Badger, P.C.,"Ethanol From Cellulose: A General Review," in: J. Janick and A. Whipkey (eds.), Trends In new crops and new uses, 2002, pp. 17-21, ASHS Press, Alexandria, VA.

Bailey, Michael J., et al,"Hydrolytic Properties of two Cellulases of *Trichoderma reesei* Expressed in Yeast," Biotechnol. Appl. Biochem., 1993, pp. 65-76, vol. 17.

Bendtsen, Jannick Dyrlov, et al.,"Improved Prediction of Signal Peptides: SignalP 3.0," J. Mol. Biol., 2004, pp. 783-795, vol. 340.

Coen, Donald M.,"Quantitation of Rare DNAs by PCR," Current Protocols in Molecular Biology, 2001, pp. 151.1-15.7.8, John Wiley & Sons, Inc.

Gellissen, Gerd,"Production of Recombinant Proteins," 2005, pp. 1-385, Wiley-VCH Verlag GmbH & Co.

Haakana, Heli, et al., "Cloning of Cellulase Genes from *Melanocarpus albomyces* and their Efficient Expression in *Trichoderma reesei*," Enzyme and Microbial Technology, 2004, pp. 159-167, vol. 34, Elsevier Inc.

Henrissat, Bernard,"A Classification of Glycosyl Hydrolases based on Amino Acid Sequence Similarities," Biochemistry Journal, 1991, pp. 309-316, vol. 280.

Henrissat, Bernard, et al.,"New Families in the Classification of Glycosyl Hydrolases based on Amino Acid Sequence Similarities," Biochemistry Journal, 1993, pp. 781-788, vol. 293.

Henrissat, Bernard, et al.,"Updating the sequence-based Classification of Glycosyl Hydrolases," Biochemistry Journal, 1996, pp. 695-696, vol. 316.

Hong, Jiong, et al., Cloning of a Gene Encoding a Thermo-stable endo-β-1,4-Glucanase from *Thermoascus aurantiacus* and its Expression in Yeast, Biotechnology Letters, Feb. 2003, pp. 657-661, vol. 25, Kluwer Academic Publishers.

Hong, Jiong, et al., Cloning of a Gene Encoding a Thermostable Cellobiohydrolase from *Thermoascus aurantiacus* and its Expression in Yeast, Appl. Microbiol. Biotechnol., Jun. 2003, pp. 42-50, vol. 63, Springer-Verlag.

Joutsjoki, Vesa V., et al.,"Transformation of *Trichoderma reesi* with the *Hormoconis resinae* Glucoamylase P (gamP) Gene: Production of a Heterologous Glucoamylase by *Trichoderma reesei*," Current Genetics, 1993, pp. 223-228, vol. 24, Springer-Verlag.

Karhunen, Taina, et al.,"High Frequency One-Step Gene Replacement in *Trichoderma reesei*. I. Endoglucanase I Overproduction," Mol. Gen. Genet., 1993, pp. 515-522, vol. 241, Springer-Verlag.

Miettinen-Oinonen, Arja, et al.,"Three Cellulases from *Melanocarpus albomyces* for Textile Treatment at Neutral pH," Enzyme and Microbial Technology, 2004, pp. 332-341, vol. 34, Elsevier Inc.

Needleman, Saul B., et al., A General Method Applicable to the Search for Similarities in the Amino Acid Sequence of Two Proteins, J. Mol. Biol., 1970, pp. 443-453, vol. 48.

Nielsen, Henrik, et al.,"Identification of Prokaryotic and Eukaryotic Signal Peptides and Prediction of their Cleavage Sites", 1997, pp. 1-6, vol. 10, No. 1, Oxford University Press.

Nielsen, Henrik, et al.,"Prediction of Signal Peptides and Signal Anchors by a Hidden Markov Model," 1998, pp. 122-130, American Association for Artificial Intelligence.

Paloheimo, Marja, et al.,"High-Yield Production of a Bacterial Xylanase in the Filamentous Fungus *Trichoderma reesei* Requires a Carrier Polypeptide with an Intact Domain Structure," Applied and Environmental Microbiology, Dec. 2003, pp. 7073-7082, vol. 69, No. 12, American Society for Microbiology.

Penttila, Merja, et al.,"A Versatile Transformation System for the Cellulolytic Filamentous Fungus *Trichoderma reesei*," Gene, 1987, pp. 155-164, vol. 61, Elsevier Science Publishers B.V.

Raeder, U., et al.,"Rapid Preparation of DNA from Filamentous Fungi," Letters in Applied Microbiology, 1985, pp. 17-20, vol. 1.

Szijarto, Nora, et al.,"Thermostable Endoglucanases in the Liquefaction of Hydrothermally Pretreated Wheat Straw," Biotechnology for Biofuels, 2011, pp. 1-10, vol. 4, No. 2.

Tuohy, Maria G., et al.,"Kinetic Parameters and Mode of Action of the Cellobiohydrolases Produced by *Talaromyces emersonii*," Biochimica et Biophysica Acta, 2002, pp. 366-380, vol. 1596, Elsevier Science B.V.

Van Tilbeurgh, Herman, et al., Flurogenic and Chromogenic Glycosides as Substrates and Ligands of Carbohydrases, Methods of Enzymology, 1988, pp. 45-59, vol. 160, Academic Press, Inc.

Visser, Hans, et al.,"Development of a Mature Fungal Technology and Production Platform for Industrial Enzymes based on a *Myceliophthora thermophila* Isolate, Previously known as *Chrysosporium lucknwense* C1," Industrial Biotechnology, Jun. 2011, pp. 214-223, vol. 7, No. 3, Mary Ann Liebert, Inc.

Voutilainen, Sanni P., et al.,"Cloning, Expression, and Characterization of Novel Thermostable Family 7 Cellobiohydrolases," Biotechnology and Bioengineering, Oct. 2008, pp. 515-528, vol. 101, No. 3, Wiley Periodicals, Inc.

Search Report issued from corresponding Finnish Patent Application No. 20125550, dated Feb. 15, 2013.

* cited by examiner

Expression cassette figure Fig. 1

Hydrolysis experiment figures Fig. 2A-B

ENDOGLUCANASES FOR TREATMENT OF CELLULOSIC MATERIAL

RELATED APPLICATION DATA

This application claims the benefit of U.S. provisional application Ser. No. 61/651,256 filed May 24, 2012, hereby incorporated by reference herein in its entirety.

The work leading to this invention has received funding from the European Community's Seventh Framework Programme FP7/2007-2013 under grant agreement no 239341.

FIELD OF THE INVENTION

The present invention relates to production of fermentable sugars from lignocellulosic material by enzymatic conversion. The fermentable sugars are useful e.g. in the production of bioethanol, or for other purposes. In particular the invention relates to novel polypeptides, polynucleotides encoding them, and to vectors and host cells containing the polynucleotides. The invention is further directed to a method for treating cellulosic material with fungal endoglucanase or an enzyme preparation containing said enzyme. Still further the invention is directed to uses of the polypeptides or enzyme preparations containing said polypeptides and to a method of preparing them.

BACKGROUND OF THE INVENTION

Limited resources of fossil fuels, and increasing amounts of $CO_2$ released from them and causing the greenhouse phenomenon have raised a need for using biomass as a renewable and clean source of energy. Biomass resources can be broadly categorized as agricultural or forestry-based, including secondary sources derived from agro and wood industries, waste sources and municipal solid wastes. One promising, alternative technology is the production of biofuels i.e. (bio)ethanol from lignocellulosic materials. In the transportation sector biofuels are for the time being the only option, which could reduce the $CO_2$ emissions by an order of magnitude. The ethanol can be used in existing vehicles and distribution systems and thus it does not require expensive infrastructure investments. Sugars derived from lignocellulosic renewable raw materials can also be used as raw materials for a variety of chemical products that can replace oil-based chemicals.

Lignocellulosic raw material comprises an abundant source of carbohydrates for a variety of biofuels, including bioethanol. Most of the carbohydrates in plants are in the form of lignocellulose, which essentially consists of cellulose, hemicellulose, and lignin. Lignocellulose can be converted into bioethanol and other chemical products via fermentation following hydrolysis to fermentable sugars. In a conventional lignocellulose-to-ethanol process the lignocellulosic material is first pretreated either chemically or physically to make the cellulose fraction more accessible to hydrolysis. The cellulose fraction is then hydrolysed to obtain sugars that can be fermented by yeast into ethanol and distilled to obtain pure ethanol. Lignin is obtained as a main co-product that may be used as a solid fuel.

One barrier of production of biofuels from cellulosic and lignocellulosic biomass is the robustness of the cell walls and the presence of sugar monomers in the form of inaccessible polymers that require a great amount of processing to make sugar monomers available to the micro-organisms that are typically used to produce alcohol by fermentation. Enzymatic hydrolysis is considered the most promising technology for converting cellulosic biomass into fermentable sugars. However, enzymatic hydrolysis is used only to a limited amount at industrial scale, and especially when using strongly lignified material such as wood or agricultural waste the technology is not satisfactory. The cost of the enzymatic step is one of the major economic factors of the process. Efforts have been made to improve the efficiency of the enzymatic hydrolysis of the cellulosic material (Badger 2002).

WO2001060752 describes a continuous process for converting solid lignocellulosic biomass into combustible fuel products. After pretreatment by wet oxidation or steam explosion the biomass is partially separated into cellulose, hemicellulose and lignin, and is then subjected to partial hydrolysis using one or more carbohydrase enzymes (EC 3.2).

WO2002024882 concerns a method of converting cellulose to glucose by treating a pretreated lignocellulosic substrate with an enzyme mixture comprising cellulase and a modified cellobiohydrolase I (CBHI) obtained by inactivating its cellulose binding domain (CBD).

US 20040005674 A1 describes novel enzyme mixtures that can be used directly on lignocellulose substrate, whereby toxic waste products formed during pretreatment processes may be avoided, and energy may be saved. The synergistic enzyme mixture contains a cellulase and an auxiliary enzyme such as xylanase, ligninase, amylase, protease, lipidase or glucuronidase, or any combination thereof. Cellulase is considered to include endoglucanase, beta-glucosidase and cellobiohydrolase. US 20050164355 describes a method for degrading lignocellulosic material with one or more cellulolytic enzymes selected from endoglucanase, beta-glucosidase and cellobiohydrolase and in the presence of at least one surfactant. Additional enzymes such as hemicellulases, esterase, peroxidase, protease, laccase or mixture thereof may also be used. The presence of surfactant increases the degradation of lignocellulosic material compared to the absence of surfactant.

WO2011080317 describes a method of treating cellulosic material with fungal CBHII/Cel6A cellobiohydrolase enzyme. The enzyme is useful in various industrial applications, particularly in production of biofuels, where production of fermentable sugars from lignocellulosic material at moderate to elevated temperature is advantageous.

Cellulases from a number of bacterial and fungal sources have been purified and characterized. The best investigated and most widely applied cellulolytic enzymes of fungal origin have been derived from *Trichoderma reesei* (the anamorph of *Hypocrea jecorina*). Cellulases from less known fungi have also been disclosed. Hong et al. (2003a and 2003b) characterize EG and CBHI of *Thermoascus aurantiacus* produced in yeast. Tuohy et al. (2002) describe three forms of cellobiohydrolases from *Talaromyces emersonii*, a moderately thermophilic fungus. The sequence and detailed biochemical characterization of these *T. emersonii* cellobiohydrolases have shown comparable properties with the cellobiohydrolases of *T. reesei* and *P. chrysosporium*. The cellulase enzymes of another thermophilic fungus, *Melanocarpus albomyces*, include at least two endoglucanases (Cel45A and Cel7A) and one cellobiohydrolase (Cel7B). These enzymes have been cloned and characterized for their pH and temperature behavior (Miettinen-Oinonen et al., 2004). WO2007071818 describes enzymatic conversion of lignocellulosic material by enzymes including cellobiohydrolase, endoglucanase, beta-glucosidase and optionally xylanase derived from *Thermoascus auranticus, Acremonium thermophilium* or *Chaetomium thermophilium*. U.S. Pat. No. 7,892,812 describes cellulose compositions comprising endoglucanase and their use in industrial applications, for example in saccharification of lignocellulose biomass.

The cellulases are from fungi *Chrysosporium lucknowense*, which has been identified as *Myceliophthora thermophila* (Visser et al., 2011).

Endoglucanases of the Cel7 family (EGs fam 7) are disclosed e.g. in U.S. Pat. No. 5,912,157, which pertains *Myceliphthora* endoglucanase and its homologues and applications thereof in detergent, textile, and pulp. U.S. Pat. No. 6,071,735 describes cellulases exhibiting high endoglucanase activity in alkaline conditions. Uses as detergent, in pulp and paper, and textile applications are discussed. U.S. Pat. No. 5,763,254 discloses enzymes from strains of *Humicola*, *Fusarium* and *Myceliopthora* degrading cellulose/hemicellulose and having a carbohydrate binding module homologous to the region A of *T. reesei*. WO2004078919 discloses purified glycosyl hydrolase family 7 (Cel7A) enzymes from *Penicillium funiculosum*, which demonstrate a high level of specific performance when formulated with an endoglucanase and tested on pretreated corn stover.

Haakana et al., (2004) describes the cloning and sequencing of three genes encoding cellulases Cel45A, Cel7A and Cel7B from *Melanocarpus albomyces*. These cellulases work well in biostoning, with lower backstaining compared to *T. reesei*. WO9714804 discloses Cel7A family enzymes from *Melanocarpus albomyces* and its applications in textile and detergent industry. Voutilainen et al., (2008) describes novel GH7 family cellobiohydrolases from the thermophilic fungi *Acremonium thermophilum*, *Thermoascus auranticus* and *Chaetomium thermophilum* active on insoluble polymeric substrates and participating in the rate limiting step in the hydrolysis of cellulose.

U.S. Pat. No. 5,393,670 describes the DNA, vectors and transformed host encoding *Trichoderma reesei* endoglucanase I.

There is a continuous need for new methods of degrading cellulosic substrates, in particular lignocellulosic substrates, and for new enzymes and enzyme mixtures, which enhance the efficiency of the degradation. There is also a need for enzymes and processes, which are versatile and which work not only at moderate temperatures but also at high temperatures, thus increasing the reaction rates and enabling the use of high biomass consistency leading to high sugar and ethanol concentrations. This approach may lead to significant savings in energy and investment costs. The high temperature also decreases the risk of contamination during hydrolysis. The present invention aims to meet at least part of these needs.

BRIEF DESCRIPTION OF THE INVENTION

It is an object of the present invention to provide novel polypeptides having endoglucanase activity and polynucleotides encoding the polypeptides. The novel polypeptides may have improved specific activity and/or improved thermostability. The novel polypeptides may also have versatile applications. A further object of the present invention is to provide new enzymes and enzyme preparations, which enhance the efficiency of the cellulosic degradation. Especially the object of the invention is to provide new enzymes having endoglucanase activity. Another object of the present invention is to provide a method for treating cellulose material with an improved enzyme or enzyme preparation.

The objects of the invention are achieved by novel polypeptides of GH family 7 (Cel7) obtained from *Acremonium thermophilum* ALKO4245.

The present invention provides a polypeptide having endoglucanase activity and comprising an amino acid sequence having at least 57% identity to SEQ ID NO:7 (EG_A) or at least 58% identity to SEQ ID NO:8 (EG_B) or a fragment or variant thereof having endoglucanase activity.

The invention further provides an isolated polynucleotide selected from the group consisting of:

a) a polynucleotide comprising the coding sequence as shown in SEQ ID NO: 5 or 6;

b) a polynucleotide encoding a polypeptide of claim 1;

c) a polynucleotide encoding a fragment of a polypeptide encoded by a polynucleotide of a) or b), wherein said fragment has endoglucanase activity; and d) a polynucleotide comprising a nucleotide sequence which is degenerate to the nucleotide sequence of a polynucleotide of a) or b);

or the complementary strand of such a polynucleotide.

The invention is also directed to a vector, which comprises said polynucleotide and a host cell comprising said vector. *Escherichia coli* strains having accession number DSM 25492, DSM 25493, DSM 25657, DSM, 25658, DSM 25655 and DSM 25656 are also included in the invention.

A further object of the invention is to provide a method of producing said polypeptide having endoglucanase activity, the method comprising the steps of transforming a host cell with an expression vector encoding said polypeptide, and culturing said host cell under conditions enabling expression of said polypeptide, and optionally recovering and purifying said polypeptide.

Other objects of the invention are the enzyme preparations comprising at least one of the novel polypeptides and the use of said enzyme preparations and polypeptides in biofuel, biomass hydrolysis, starch, textile, detergent, pulp and paper, food, feed or beverage industry.

The invention also provides a method for treating cellulosic material with an endoglucanase or an enzyme preparation comprising said endoglucanase, wherein the method comprises the following steps:

i) reacting the cellulosic material with said endoglucanase or the enzyme preparation comprising said endoglucanase ii) obtaining at least partially hydrolyzed cellulosic material.

Specific embodiments of the invention are set forth in the dependent claims. Other objects, details and advantages of the present invention will become apparent from the following drawings, detailed description and examples.

The novel endoglucanase applicable in the method is capable of hydrolysing cellulosic materials at moderate to elevated temperatures, particularly in combination with other enzymes used in hydrolysis of cellulosic or lignocellulosic materials.

Endoglucanases obtainable from *Acremonium thermophilum* ALKO4245 are particularly useful in hydrolysing and degrading cellulosic material. The enzymes are kinetically very effective over a broad range of temperatures, and although they have high activity at standard hydrolysis temperatures, they are also very efficient at high temperatures. This makes them extremely well suited for varying cellulosic substrate hydrolysis processes carried out both at conventional temperatures and at elevated temperatures. In the conventional separate hydrolysis and fermentation process (SHF) the temperature of enzymatic hydrolysis is typically higher than that of fermentation. The use of thermostable enzymes in the hydrolysis offer potential benefits, such as higher reaction rates at elevated temperatures, reduction of enzyme load due to higher specific activity and stability of enzymes, increased flexibility with respect to process configuration and decreased contamination risk. The general robustness of thermostable enzymes compared to mesophilic ones also increases the recyclability of enzymes in the industrial process.

BRIEF DESCRIPTION OF THE DRAWINGS

In the following the invention will be described in greater detail by means of preferred embodiments with reference to the attached drawings, in which FIG. 1 schematically shows the expression cassettes used in the transformation of *Trichoderma reesei* protoplasts for overproducing the recombinant *Acremonium thermophilum* ALKO4245 EG/Cel7 proteins (EG_A and EG_B), *Acremonium thermophilum* ALKO4245 EG/Cel7+*Trichoderma reesei* EGI/Cel7B_linker-CBM (EG_A+EGI-CBM and EG_B+EGI-CBM) and *Acremonium thermophilum* ALKO4245 EG/Cel7+*Trichoderma reesei* CBHI/Cel7A_linker-CBM (EG_A+CBHI-CBM and EG_B+CBHI-CBM) fusion proteins. The *Acremonium thermophilum* ALKO4245 cel7/egl genes (egl_A and egl_B) and cel7/egl-CBM fusion genes *Acremonium thermophilum* ALKO4245 cel7/egl+*Trichoderma reesei* cel7B/egl1_linker-CBM (egl_A+egl1-CBM and egl_B+egl1-CBM) and *Acremonium thermophilum* ALKO4245 cel7/egl+*Trichoderma reesei* cel7A/cbh1_linker-CBM (egl_A+cbh1-CBM and egl_B+cbh1-CBM) were under the control of *T. reesei* cel7A/cbh1 promoter (p cbh1) and the termination of the transcription was ensured by using *T. reesei* cel7A/cbh1 terminator sequence (t cbh1). The amdS gene was included as a transformation marker.

FIG. 2A shows the hydrolysis results of steam exploded corn fibre performed at 37° C. with a basis enzyme mixture (MIXTURE 1) supplemented with the EG_A (MIXTURE 1_EG_A) or EG_B (MIXTURE 1_EG_B).

FIG. 2B shows the hydrolysis results of steam exploded corn fibre performed at 55° C. with a basis enzyme mixture (MIXTURE 1) supplemented with the EG_A (MIXTURE 1_EG_A).

FIG. 3A shows the hydrolysis results of steam exploded corn fibre performed at 37° C. with low dry matter conditions and with a basis enzyme mixture (MIXTURE 1) supplemented with the EG_A+EGI-CBM or EG_B+EGI-CBM.

FIG. 3B shows the hydrolysis results of steam exploded corn fibre performed at 37° C. with high dry matter conditions and with a basis enzyme mixture (MIXTURE 1) supplemented with the EG_B+EGI-CBM.

FIG. 3C shows the hydrolysis results of steam exploded corn fibre performed at 55° C. with high dry matter conditions and with a basis enzyme mixture (MIXTURE 1) supplemented with the EG_B+EGI-CBM.

FIG. 4A shows the hydrolysis results of steam exploded corn fibre performed at 37° C. with low dry matter conditions and with a basis enzyme mixture (MIXTURE 1) supplemented with the EG_A+CBHI-CBM or EG_B+CBHI-CBM.

FIG. 4B shows the hydrolysis results of steam exploded corn fibre performed at 37° C. with high dry matter conditions and with a basis enzyme mixture (MIXTURE 1) supplemented with the EG_A+CBHI-CBM or EG_B+CBHI-CBM.

FIG. 4C shows the hydrolysis results of steam exploded corn fibre performed at 55° C. with high dry matter conditions and with a basis enzyme mixture (MIXTURE 1) supplemented with the EG_B+CBHI-CBM.

SEQUENCE LISTING

Figure 1:
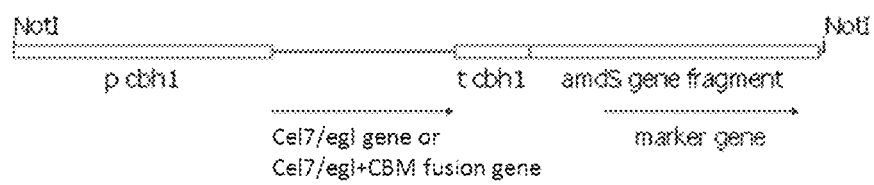

SEQ ID NO: 1 Sequence of the oligonucleotide primer egl9

SEQ ID NO: 2 Sequence of the oligonucleotide primer egl11

SEQ ID NO: 3 Sequence of the PCR fragment obtained from *Acremonium thermophilum* ALKO4245 (CBS 116240) using the primers egl9 and egl11.

SEQ ID NO: 4 Sequence of the PCR fragment obtained from *Acremonium thermophilum* ALKO4245 (CBS 116240) using primers egl9 and egl11.

SEQ ID NO: 5 The nucleotide sequence of the *Acremonium thermophilum* ALKO4245 (CBS 116240) egl_A gene.

SEQ ID NO: 6 The nucleotide sequence of the *Acremonium thermophilum* ALKO4245 (CBS 116240) egl_B gene.

SEQ ID NO: 7 The deduced amino acid sequence of the *Acremonium thermophilum* ALKO4245 (CBS 116240) EG_A.

SEQ ID NO: 8 The deduced amino acid sequence of the *Acremonium thermophilum* ALKO4245 (CBS 116240) EG_B.

SEQ ID NO: 9 Sequence of the oligonucleotide primer egl50

SEQ ID NO: 10 Sequence of the oligonucleotide primer CBM_1

SEQ ID NO: 11 Sequence of the oligonucleotide primer CBM_2

SEQ ID NO: 12 Sequence of the oligonucleotide primer CBM_17

SEQ ID NO: 13 Sequence of the oligonucleotide primer egl64

SEQ ID NO: 14 Sequence of the oligonucleotide primer CBM_4

SEQ ID NO: 15 Sequence of the oligonucleotide primer CBM_5

SEQ ID NO: 16 Sequence of the oligonucleotide primer CBM_18

SEQ ID NO: 17 Sequence of the PCR fragment obtained from a plasmid containing the full-length *Acremonium thermophilum* ALKO4245 egl_A gene using primers egl50 and CBM_1.

SEQ ID NO: 18 Sequence of the PCR fragment obtained from a plasmid containing the full-length *Acremonium thermophilum* ALKO4245 egl_B gene using primers egl64 and CBM_4.

SEQ ID NO: 19 Sequence of the PCR fragment obtained from plasmid containing the *Trichoderma reesei* egl1 gene using primers CBM_2 and CBM_17.

SEQ ID NO: 20 Sequence of the PCR fragment obtained from plasmid containing the *Trichoderma reesei* egl1 gene using primers CBM_5 and CBM_18.

SEQ ID NO: 21 The nucleotide sequence of the *Acremonium thermophilum* ALKO4245 (CBS 116240) egl_A+*Trichoderma reesei* egl1-CBM fusion gene.

SEQ ID NO: 22 The nucleotide sequence of the *Acremonium thermophilum* ALKO4245 (CBS 116240) egl_B+*Trichoderma reesei* egl1-CBM fusion gene.

SEQ ID NO: 23 The deduced amino acid sequence of the *Acremonium thermophilum* ALKO4245 (CBS 116240) EGA+*Trichoderma reesei* EGI-CBM fusion protein.

SEQ ID NO: 24 The deduced amino acid sequence of the *Acremonium thermophilum* ALKO4245 (CBS 116240) EG_B+*Trichoderma reesei* EGI-CBM fusion protein.

SEQ ID NO: 25 The nucleotide sequence of the *Acremonium thermophilum* ALKO4245 (CBS 116240) egl_A+*Trichoderma reesei* cbh1-CBM fusion gene.

SEQ ID NO: 26 The nucleotide sequence of the *Acremonium thermophilum* ALKO4245 (CBS 116240) egl_B+*Trichoderma reesei* cbh1-CBM fusion gene.

SEQ ID NO: 27 The deduced amino acid sequence of the *Acremonium thermophilum* ALKO4245 (CBS 116240) EGA+*Trichoderma reesei* CBHI-CBM fusion protein.

SEQ ID NO: 28 The deduced amino acid sequence of the *Acremonium thermophilum* ALKO4245 (CBS 116240) EG_B+*Trichoderma reesei* CBHI-CBM fusion protein.

DETAILED DESCRIPTION OF THE INVENTION

Cellulose is the major structural component of higher plants. It provides plant cells with high tensile strength helping them to resist mechanical stress and osmotic pressure. Cellulose is a β-1,4-glucan composed of linear chains of glucose residues joined by β-1,4-glycosidic linkages. Cellobiose is the smallest repeating unit of cellulose. In cell walls cellulose is packed in variously oriented sheets, which are embedded in a matrix of hemicellulose and lignin. Hemicellulose is a heterogeneous group of carbohydrate polymers containing mainly different glucans, xylans and mannans. Hemicellulose consists of a linear backbone with β-1,4-linked residues substituted with short side chains usually containing acetyl, glucuronyl, arabinosyl and galactosyl. Hemicellulose can be chemically cross-linked to lignin. Lignin is a complex cross-linked polymer of variously substituted p-hydroxyphenylpropane units that provides strength to the cell wall to withstand mechanical stress, and it also protects cellulose from enzymatic hydrolysis.

"Cellulose" or "cellulosic material" as used herein, relates to any material comprising cellulose, hemicellulose and/or lignocellulose as a significant component. Examples of cellulosic material include textile fibers derived e.g. from cotton, flax, hemp, jute and the man-made cellulosic fibers as modal, viscose and lyocel.

"Lignocellulose" is a combination of cellulose and hemicellulose and polymers of phenol propanol units and lignin. It is physically hard, dense, and inaccessible and the most abundant biochemical material in the biosphere. "Lignocellulosic material" means any material comprising lignocellulose. Such materials are for example: hardwood and softwood chips, wood pulp, sawdust and forestry and wood industrial waste; agricultural biomass as cereal straws, sugar beet pulp, corn fibre, corn stover and corn cobs, sugar cane bagasse, stems, leaves, hulls, husks, and the like; waste products as municipal solid waste, newspaper and waste office paper, milling waste of e.g. grains; dedicated energy crops (e.g., willow, poplar, swithcgrass or reed canarygrass, and the like). Preferred examples are corn stover, switchgrass, cereal straw, sugarcane bagasse and wood derived materials.

Cellulosic material is degraded in nature by a number of various organisms including bacteria and fungi which produce enzymes capable of hydrolyzing carbohydrate polymers. Degradation usually requires different cellulases acting sequentially or simultaneously. Degradation of more complex cellulose containing substrates requires a broad range of various enzymes. For example hemicellulose is degraded by hemicellulases, like xylanases and mannanases. Hemicellulase is an enzyme hydrolysing hemicellulose.

"Cellulolytic enzymes" are enzymes having "cellulolytic activity", which means that they are capable of hydrolysing cellulosic substrates or derivatives thereof into smaller saccharides. Cellulolytic enzymes thus include both cellulases and hemicellulases. Cellulases as used herein include (1) endoglucanases (EG, EC 3.2.1.4) which cut internal beta-1,4-glucosidic bonds; (2) exoglucanases or cellobiohydrolases (CBH, EC 3.2.1.91) that cut the di-saccharide cellobiose from the reducing or non-reducing end of the crystalline cellulose polymer chain; (3) beta-1,4-glucosidases (BG, EC 3.2.1.21) which hydrolyze the cellobiose and other short cellooligosaccharides to glucose. The CAZY (carbohydrate active enzymes) classification system collates glycosyl hydrolase (GH) enzymes into families according to sequence similarity, which have been shown to reflect shared structural features. In addition to this cellulases can be classified to various glycosyl hydrolase families according their primary sequence, supported by analysis of the three dimensional structure of some members of the family (Henrissat 1991, Henrissat and Bairoch 1993, 1996).

*T. reesei* has a well-known and effective cellulase system containing two CBH's, two major and several minor EG's and several BG's. *T. reesei* CBHI (Cel7A) cuts sugar from the reducing end of the cellulose chain, has a C-terminal cellulose binding module (CBM) and may constitute up to 60% of the total secreted protein. *T. reesei* CBHII (Cel6A) cuts sugar from the non-reducing end of the cellulose chain, has an N-terminal cellulose binding module and may constitute up to 20% of the total secreted protein. Endoglucanases EGI (Cel7B), and EGV (Cel45A) have a cellulose binding module (CBM) in their C-terminus, EGII (Cel5A) has an N-terminal CBM and EGIII (Cel12A) does not have a cellulose binding module at all. CBHI, CBHII, EGI and EGII are so called "major cellulases" of *Trichoderma* comprising together 80-90% of total secreted proteins. It is known to a man skilled in the art that an enzyme may be active on several substrates and enzymatic activities can be measured using different substrates, methods and conditions. Identifying different cellulolytic activities is discussed for example in van Tilbeurgh et al. 1988.

Many fungal hydrolases are modular proteins, and all of them contain a catalytic domain (CD)/core expressing cellulolytic activity. In addition to the CD, hydrolases may contain a carbohydrate binding module, also named as cellulose binding domain (CBD), which can be located either at the N- or C-terminus of the catalytic domain. CBM mediates the binding of the cellulase to crystalline cellulose but has little or no effect on cellulase hydrolytic activity of the enzyme on soluble substrates. These two domains are typically connected via a flexible and highly glycosylated linker region.

Glycoside hydrolase family 7 (GH7) comprises enzymes with several known activities, especially endoglucanase and cellobiohydrolase. "Endoglucanases (EG)" are enzymes that cut internal glycosidic bonds of the cellulose chain. They are 1,4-beta-D-glucan 4-glucanohydrolases and catalyze endohydrolysis of 1,4-beta-D-glycosidic linkages in polymers of glucose such as cellulose and derivatives thereof. Some endoglucanases have a naturally occurring cellulose binding domain, while others do not. Some endoglucanases have also xylanase activity (Bailey et al., 1993).

The present invention is based on studies, which attempted to find novel GH7 family endoglucanases which would improve hydrolysis efficiency of cellulosic substrates and which could be used for versatile applications. The identification of the novel enzymes was done using known molecular biology methods. The basic methods are described, for example, in Sambrook and Russel, 2001. Two GH family 7 (Cel7) endoglucanases referred as EG_A and EG_B were obtained (Table 1).

TABLE 1

The EG/Cel7 endoglucanases of the invention

| Endoglucanase | nucleic acid SEQ ID NO: | amino acid SEQ ID NO: | accession nr for the deposition |
|---|---|---|---|
| EG_A | 5 | 7 | 25492 |
| EG_B | 6 | 8 | 25493 |

The novel EG/Cel7 endoglucanases according to the present invention are obtainable from *Acremonium* sp. preferably from *Acremonium thermophilium* and more preferably from strain having the characteristics of strain ALKO4245 deposited as CBS 116240. "Obtainable from" means that they can be obtained from said species, but it does not exclude the possibility of obtaining them from other sources. In other words they may originate from any organism including plants. Preferably they originate from microorganisms e.g. bacteria or fungi. The bacteria may be for example from a genus selected from *Bacillus, Azospirillum* and *Streptomyces*. More preferably the enzyme originates from fungi (including filamentous fungi and yeasts), for example from a genus selected from the group consisting of *Thermoascus, Acremonium, Chaetomium, Achaetomium, Thielavia, Aspergillus, Botrytis, Chrysosporium, Collybia, Fomes, Fusarium, Humicola, Hypocrea, Lentinus, Melanocarpus, Myceliophthora, Myriococcum, Neurospora, Penicillium, Phanerochaete, Phlebia, Pleurotus, Podospora, Polyporus, Rhizoctonia, Scytalidium, Pycnoporus, Talaromyces, Trametes* and *Trichoderma*.

The novel EG/Cel7 polypeptides of the invention having endoglucanase activity preferably comprise an amino acid sequence having at least 57% identity to SEQ ID NO:7 (EG_A) or at least 58% identity to SEQ ID NO:8 (EG_B) or a fragment or variant thereof having endoglucanase activity. According to one embodiment of the invention, the polypeptide has at least 60, 65, 70, 75, 80, 85, 90, 95, 98 or 99% identity to SEQ ID NO: 7 or 8 or to its enzymatically active fragment. The EG/Cel7 polypeptides having endoglucanase activity are also herein simply called endoglucanases.

By the term "identity" is here meant the global identity between two amino acid sequences compared to each other from the first amino acid encoded by the corresponding gene to the last amino acid. The identity of the full-length sequences is measured by using EMBOSS Needle Needleman-Wunsch global alignment program at EBI (European Bioinformatics Institute) http://www.ebi.ac.uk/Tools/psa/emboss_needle/ with the following parameters: BLOSUM50, Gap open 10.0, Gap extend 0.5. The algorithm is described in Needleman and Wunsch (1970). The man skilled in the art is aware of the fact that results using Needleman-Wunsch algorithm are comparable only when aligning corresponding domains of the sequence and using the same parameters in each comparison. Consequently comparison of e.g. cellulase sequences including CBM or signal sequences with sequences lacking those elements cannot be done.

By the term "fragment having endoglucanase activity" is meant any fragment of a defined sequence that has endoglucanase activity. In other words a fragment having endoglucanase activity may be the mature protein part of the defined sequence, or it may be only a fragment of the mature protein part, provided that it still has endoglucanase activity.

The novel polypeptides may also be variants of said polypeptides. A "variant" may be a polypeptide that occurs naturally e.g. as an allelic variant within the same strain, species or genus, or it may have been generated by mutagenesis. It may comprise amino acid substitutions, deletions or insertions, but it still functions in a substantially similar manner to the enzymes defined above i.e. it comprises a fragment having endoglucanase activity.

The cellulolytic polypeptides are usually produced in the cell as prepolypeptides comprising a signal sequence that is cleaved off during secretion of the protein. They may also be further processed during secretion both at the N-terminal and/or C-terminal end to give a mature, enzymatically active protein. "A polypeptide having endoglucanase activity" thus denotes that the polypeptide may be either in immature or mature form, preferably it is in mature form, i.e. the processing has taken place. In addition, the "mature form" means an enzyme which has been cleaved from its carrier protein in fusion constructions.

The EG/Cel7 endoglucanases of the present invention are preferably recombinant enzymes, which may be produced in a generally known manner. A polynucleotide fragment comprising the endoglucanase gene is isolated, the gene is inserted under a strong promoter into an expression vector, the vector is transformed into suitable host cells and the host cells are cultivated under conditions provoking production of the enzyme. Methods for protein production by recombinant technology in different host systems are well known in the art (Sambrook et al., 1989; Coen, 2001; Gellissen, 2005). Preferably the enzymes are produced as extracellular enzymes that are secreted into the culture medium, from which they can easily be recovered and isolated.

The recombinant polypeptide may be a fused polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator.

The polypeptide of the invention disclosed in SEQ ID NO: 7 naturally contains a C-terminal CBM and a linker. "A linker" is a flexible and highly glycosylated region which connects the catalytic domain and the CBM. As used herein the CBM includes also the linker region. In one embodiment of the invention this native linker and CBM region may be replaced by, e.g. a linker and a CBM from a *Trichoderma* or *Chaetomium* species, preferably from *Trichoderma reesei*. In a preferred embodiment the natural CBM of endoglucanase EG_A has been replaced with a CBM of *T. reesei* endoglucanase I (EGI/Cel7B) or a CBM of *T. reesei* cellobiohydrolase I (CHBI/Cel7A) and preferably the resulting fusion protein comprises an amino acid sequence having SEQ ID NO: 23 (EG_A+EGI-CBM) or SEQ ID NO:27 (EG_A+CHBI-CBM) (Table 2).

The polypeptide of the invention disclosed in SEQ ID NO: 8 does not naturally contain a CBM and a linker. In one embodiment of the invention this polypeptide may be attached by, e.g. a linker and a CBM regions from a *Trichoderma* or *Chaetomium* species, preferably from *Trichoderma reesei*. In a preferred embodiment the linker and CBM of *T. reesei* EGI/Cel7B or *T. reesei* CHBI/Cel7A has been genetically attached to the endoglucanase EG_B and preferably the resulting fusion protein comprises an amino acid sequence having SEQ ID NO: 24 (EG_B+EGI-CBM) or SEQ ID NO: 28 (EG_B+CHBI-CBM) (Table 2).

TABLE 2

EG + CBM recombinant fusion proteins of the invention

| EG + CBM fusion protein | nucleic acid SEQ ID NO: | amino acid SEQ ID NO: | accession nr for the deposition |
|---|---|---|---|
| EG_A + EGI-CBM | 21 | 23 | DSM 25657 |
| EG_B + EGI-CBM | 22 | 24 | DSM 25658 |
| EG_A + CBHI-CBM | 25 | 27 | DSM 25655 |
| EG_B + CBHI-CBM | 26 | 28 | DSM 25656 |

Further, within the scope of the invention are recombinant fusion proteins comprising an amino acid sequence having at least 55% sequence identity to SEQ ID NO: 23 (EG_A+EGI-CBM) or SEQ ID NO: 27 (EG_A+CHBI-CBM), or at least 64% sequence identity to SEQ ID NO: 24 (EG_B+EGI-CBM) or SEQ ID NO: 28 (EG_B+CHBI-CBM). According to one embodiment of the invention the fusion protein comprises an amino acid sequence having at least 60, 65, 70, 75, 80, 85, 90, 95, 98 or 99% identity to SEQ ID NO: 23 or 27, or at least 65, 70, 75, 80, 85, 90, 95, 98 or 99% identity SEQ ID NO: 24 or 28 or to its enzymatically active fragment.

The EG/Cel7 endoglucanases of the invention may be used without a signal sequence and/or CBM or the signal sequence and/or CBM may derive from different enzymes of the above mentioned microorganisms or different microorganism or be synthetically or recombinantly incorporated to the catalytic domain of the above enzymes.

The invention relates to novel polynucleotides which may comprise a nucleotide sequence of SEQ ID NO: 5 or 6, or a sequence encoding a novel polypeptide as defined above, including complementary strands thereof. "Polynucleotide" as used herein refers to both RNA and DNA, and it may be single stranded or double stranded. Further the polynucleotide may be degenerate as a result of the genetic code to any one of the sequences as defined above. This means that different codons may code for the same amino acid.

One embodiment of the invention is an EG/Cel7 endoglucanase which is encoded by a polynucleotide sequence included in SEQ ID NO: 21, 22, 25 or 26.

The polynucleotide may also be a fragment of said polynucleotides comprising at least 17 nucleotides, preferably at least 20, 30, 40 or 50 nucleotides. According to one embodiment of the invention the polynucleotide is having a sequence set forth as SEQ ID NO 1, 2, 9, 10, 13 or 14.

According to another embodiment of the invention, the polynucleotide comprises a gene similar to that included in a microorganism having accession number DSM 25492, DSM 25493, DSM 25657, DSM 25658, DSM 25655 or DSM 25656 (Table 1, Table 2).

The EG/Cel7 endoglucanase of the invention may be produced from a recombinant expression "vector" comprising the nucleic acid molecule, which encodes the endoglucanase as characterized above, operably linked to regulatory sequences capable of directing the expression of a gene encoding said endoglucanase in a suitable host. Said regulatory sequences may be homologous or heterologous to the production organism or they may originate from the organism, from which the gene encoding the endoglucanase polypeptide of the invention is isolated. The expression vector may further comprise marker genes for selection of the transformant strains or the selection marker may be introduced to the host in another vector construct by co-transformation.

The production "host" can be any homologous or heterologous organism capable of expressing the cellulolytic enzyme. Preferably the host is a microbial cell, more preferably a fungus. Most preferably the host is a filamentous fungus. Preferred hosts for producing the cellulolytic enzymes are in particular strains from the genus *Trichoderma* or *Aspergillus*. Preferably the recombinant host is modified to express and secrete cellulolytic enzymes as its main activity or one of its main activities. This can be done by deleting genes encoding major homologous secreted enzymes e.g. the four major cellulases of *Trichoderma* and by integrating heterologous genes to a locus with high expression and production levels.

The present invention relates also to a method for producing a polypeptide having endoglucanase activity, said method comprising the steps of transforming a host cell with an expression vector encoding said polypeptide, and culturing said host cell under conditions enabling expression of said polypeptide, and optionally recovering and purifying said polypeptide. The production medium may be a medium suitable for growing the host organism and containing inducers for efficient expression.

The polypeptides of the present invention may be isolated, which in the present context may simply mean that the cells and cell debris have been removed from the culture medium containing the polypeptide. Conveniently the polypeptides are isolated e.g. by adding anionic and/or cationic polymers (flocculants) to the spent culture medium to enhance precipitation of cells and cell debris. The medium is then filtrated using an inorganic filtering agent and a filter to remove the precipitants formed. After this the filtrate is further processed using a semipermeable membrane to remove excess of salts, sugars and metabolic products. The polypeptides can also be purified or concentrated by crystallization.

The novel EG/Cel7 polypeptides obtained by the method of the present invention may be components of an enzyme preparation. The term "enzyme preparation" denotes to a composition comprising at least one of the novel polypeptides described herein. The polypeptide in the enzyme preparation may be a recombinant protein having endoglucanase activity and comprising an amino acid sequence having at least 57% sequence identity to EG_A having SEQ ID NO: 7 or at least 58% sequence identity to EG_B having SEQ ID NO: 8. In one embodiment the enzyme preparation comprises a polypeptide which is a recombinant fusion protein having at least 55% sequence identity to SEQ ID NO: 23 (EG_A+EGI-CBM) or SEQ ID NO: 27 (EG_A+CHBI-CBM), or at least 64% sequence identity to SEQ ID NO: 24 (EG_B+EGI-CBM) or SEQ ID NO: 28 (EG_B+CHBI-CBM). According to one embodiment of the invention the enzyme preparation comprises a polypeptide having at least 60, 65, 70, 75, 80, 85, 90, 95, 98 or 99% identity to SEQ ID NO: 23 or 27, or at least 65, 70, 75, 80, 85, 90, 95, 98 or 99% identity SEQ ID NO: 24 or 28 or to its enzymatically active fragment. Preferably the enzyme preparation comprises at least cellobiohydrolase, endoglucanase, beta-glucosidase and optionally xylanase.

The enzyme preparation may also comprise at least one further enzyme selected from a group of cellobiohydrolase, endoglucanase, beta-glucosidase, beta-glucanase, xyloglucanase, xylanase, beta-xylosidase, mannanase, beta-mannosidase, α-glucuronidase, acetyl xylan esterase, α-arabinofuranosidase, α-galactosidase, pectinase, involving endo- and exo-α-L-arabinases, endo- and exo-galactoronase, endopectinlyase, pectate lyase, and pectinesterase, phenol esterase, ligninase involving lignin peroxidase, manganese-dependent peroxidase, $H_2O_2$-generating enzyme and laccase with or without a mediator. The enzyme preparation may contain any combination of these enzymes and EG/Cel7 endoglucanases of the invention, but the enzymes are not limited to those described herein. They can for example also be commercially available enzyme preparations.

The enzyme preparation may be in the form of liquid, powder or granulate. It may be a filtrate containing one or more cellulolytic enzymes. Preferably the enzyme preparation is a spent culture medium. "Spent culture medium" refers to the culture medium of the host comprising the produced enzymes. Preferably the host cells are separated from the said medium after the production. The enzyme preparation or composition may also be a "whole culture broth" obtained, optionally after inactivating the production host(s) or microorganism(s) without any biomass separation, downstream processing or purification of the desired cellulolytic enzyme(s). In the consolidated bioprocess the enzyme composition or at least some of the enzymes of the enzyme composition may be produced by the fermentative microorganism.

The enzyme preparation may contain the enzymes in at least partially purified and isolated form. It may even essentially consist of the desired enzyme or enzymes. The culture medium with or without host cells may be utilized as an enzyme preparation as such without further purification, because the endoglucanase proteins can be secreted into the culture medium, and they display activity in the ambient conditions of the spent culture medium.

In addition to the endoglucanase proteins, the enzyme preparation of the invention may contain additives, such as mediators, stabilizers, buffers, preservatives, surfactants and/or culture medium components. Preferred additives are such, which are commonly used in enzyme preparations intended for a particular application.

In the method of the present application for treating cellulosic material the cellulosic material is reacted with the EG/Cel7 endoglucanase of the invention or the enzyme preparation comprising said endoglucanase, whereby at least partially hydrolyzed cellulosic material is obtained. The enzymes are added in an enzymatically effective amount either simultaneously e.g. in the form of an enzyme mixture, or sequentially, or are produced by the fermented microorganisms or as combination of these methods The EG/Cel7 endoglucanases of the invention are capable of hydrolyzing cellulosic material at moderate to elevated temperatures. The term "moderate temperature" or "conventional temperature" in context of the present invention means temperatures commonly used in cellulose hydrolysis and corresponding to the optimal temperatures or thermal stabilities of the enzymes used in such processes. Thus, the terms refer to temperature ranges from 30° C. to 45° C. The term "elevated temperature" or "high temperature" refers to temperature ranges from 45° C. to 70° C. In short term hydrolysis processes the enzymes may be effective even up to 80° C. Enzymes active or stable at such elevated temperature ranges are also called "thermostable" or "thermophilic" enzymes. The endoglucanases of the invention are used preferably at temperatures between 35° C. and 60° C. More preferably they are used at temperatures between 37° C. and 55° C., most preferably at temperatures between 45° C. and 55° C.

The EG/Cel7 endoglucanases of the invention show improved hydrolysis results both at moderate and elevated temperatures when compared to the enzyme mixtures containing conventional *T. reesei* endoglucanase EGI/Cel7B. Different enzyme mixtures and combinations may be used to suit different process conditions. Elevated temperatures are known to enhance the hydrolysis of crystalline cellulose present in cellulosic or lignocellulosic materials, thus reducing the total amount of enzymes needed in hydrolysis or reducing the required hydrolysis time. Also, since at elevated temperatures the viscosity of the lignocellulosic substrate is decreased, thermostable enzymes make it possible to work at higher solid loadings and save in investment costs.

Particularly improved results at elevated temperatures may be obtained when using an enzyme preparation comprising recombinant endoglucanase EG_A having at least 57% sequence identity to SEQ ID NO: 7. In one preferred embodiment of the invention the enzyme preparation comprises *Acremonium thermophilum* cellobiohydrolase CBHI/Cel7A, *Acremonium thermophilum* cellobiohydrolase CBHII/Cel6A, *Thermoascus aurantiacus* endoglucanase EGII/Cel5A, *Acremonium thermophilum* beta-glucosidase βG/Cel3A, *Thermoascus aurantiacus* xylanase Xyn10A and endoglucanase EG_A of the present invention.

In one embodiment of the invention the enzyme preparation comprises recombinant EG_A or EG_B fusion proteins having SEQ ID NOs: 23, 24, 27 or 28. With these endoglucanases improved hydrolysis results also at moderate and elevated temperatures with high dry matter conditions were obtained.

In one preferred embodiment of the invention the enzyme preparation comprises cellobiohydrolase CBHI/Cel 7A, cellobiohydrolase CBHII/Cel6A, endoglucanase EGII/Cel5A, beta-glucosidase βG/Cel3A, xylanase Xyn10A and endoglucanase fusion protein comprising an amino acid sequence having SEQ ID NO: 24.

In another preferred embodiment of the invention the enzyme preparation comprises cellobiohydrolase CBHI/Cel 7A, cellobiohydrolase CBHII/Cel6A, endoglucanase EGII/Cel5A, beta-glucosidase βG/Cel3A, xylanase Xyn10A and endoglucanase fusion protein comprising an amino acid sequence having SEQ ID NO: 27.

In another preferred embodiment the enzyme preparation comprises cellobiohydrolase CBHI/Cel 7A, cellobiohydrolase CBHII/Cel6A, endoglucanase EGII/Cel5A, beta-glucosidase βG/Cel3A, xylanase Xyn10A and endoglucanase fusion protein comprising an amino acid sequence having SEQ ID NO: 28.

As will be understood by one skilled in the art, any quantity of the cellulosic material may be used in the hydrolysis. The term "dry matter" as used herein refers to total solids, both soluble and insoluble, of cellulosic material. The hydrolysis of cellulosic material may be conducted at low dry matter conditions, whereby by low dry matter is <15%. In other embodiments enzymatic hydrolysis may be conducted at high dry matter content, preferably >15% dry matter.

The method for treating cellulosic material with the endoglucanases of the invention is especially suitable for producing fermentable sugars from lignocellulosic material. The fermentable sugars may then be fermented by yeast into ethanol, and used as fuel. They can also be used as intermediates or raw materials for the production of various chemicals or building blocks for the processes of chemical industry, e.g. in so called biorefinery. The lignocellulosic material may be pretreated before the enzymatic hydrolysis to disrupt the fiber structure of cellulosic substrates and make the cellulose fraction more accessible to the cellulolytic enzymes. Current pretreatments include mechanical, chemical or thermal processes and combinations thereof. The material may for example be pretreated by steam explosion or acid hydrolysis.

The novel EG/Cel7 endoglucanases may be applied in any process involving cellulolytic enzymes, such as in biofuel, biomass hydrolysis, starch, textile, detergent, pulp and paper, food, feed or beverage industry, and especially in hydrolysing cellulosic material for the production of biofuel comprising ethanol. In the pulp and paper industry they may be used to modify cellulosic fibre for example in treating kraft pulp, mechanical pulp, or recycled paper.

The invention is described by the following non-limiting examples. It will be obvious to a person skilled in the art that, as the technology advances, the inventive concept can be implemented in various ways. The invention and its embodiments are not limited to the examples described but may vary within the scope of the claims.

EXAMPLES

Example 1

Cloning of the Endoglucanase (cel7/egl) Genes

Standard molecular biology methods were used in the isolation and enzyme treatments of DNA (e.g. isolation of plasmid DNA, digestion of DNA to produce DNA fragments), in E. coli transformations, sequencing etc. The basic methods used were either as described by the enzyme, reagent or kit manufacturer or as described in the standard molecular biology handbook, e. g. Sambrook and Russell (2001). Isolation of genomic DNA was performed as described in detail by Raeder and Broda (1985).

After screening of several strains from Roal Oy culture collection one thermophilic fungal strain was selected for cloning. The probes for cloning the cel7/egl genes (egl_A and egl_B) from Acremonium thermophilum ALKO4245 were synthesized by PCR. Degenerate oligos were planned basing on the alignment of the previously published amino acid sequences of GH family 7 endoglucanase (EGI) proteins. The sequences of the primers are shown in Table 3 (SEQ ID NOs: 1-2).

TABLE 3

The oligonucleotides used as PCR primers to amplify probes for screening of egl genes from Acremonium thermophilum ALKO4245

| Template, genomic DNA from | Oligo- nucle- otides | Length (bp) | Sequence [a] | SEQ ID NO: |
|---|---|---|---|---|
| ALKO4245 | egl9_s | 20 | TGYTGYAAYGARATGGAYAT (s) | 1 |
| ALKO4245 | egl11_as | 17 | SWRTCNARCCARTTCAT (as) | 2 |

[a] N = A or G or T or C, Y = T or C, R = A or G, S = G or C, W = A or T; "s" in the parenthesis = sense strand, "as" in the parenthesis = antisense strand.

The probes were amplified by PCR with primers described in Table 3 using the genomic DNA as a template in the reactions. The PCR mixtures of Acremonium thermophilum ALKO4245 contained 1×F-511 Buffer for Dynazyme DNA Polymerase (Finnzymes, Finland), 0.2 mM dNTP Mix (Fermentas, Finland), 1 µM each primer, 3% DMSO (Finnzymes, Finland) 2-4 units of F-501L Dynazyme II DNA Polymerase (Finnzymes, Finland) and 1-2 µg of the conesponding genomic DNA. The conditions for the PCR reactions were the following: 5 min initial denaturation at 95° C., followed by 28 cycles of 1 min at 95° C., 30 sec annealing at 50° C., 30 sec extension at 72° C. and a final extension at 72° C. for 5 min.

Primer combinations described in Table 3 produced specific DNA products having the expected sizes (according to calculations basing on published cel7/egl sequences). The DNA products were isolated and purified from the PCR reaction mixtures and cloned into pCR4®4Blunt-TOPO® vectors according to the manufacturer's instructions (Invitrogen, USA). The inserts were characterized by sequencing and by performing Southern blot hybridizations to the genomic DNA digested with several restriction enzymes. The PCR fragments which were chosen to be used as probes for gene cloning from Acremonium thermophilum ALKO4245 strain are presented in Table 4.

TABLE 4

The primers used in the PCR reactions, probes chosen for screening of the egl genes from Acremonium thermophilum ALKO4245. The genomic template DNA and the name of the plasmid containing the probe fragment are shown.

| Gene | Forward primer | Reverse primer | Genomic DNA used as a template in PCR reactions | Fragment obtained (kb) | Insert in plasmid | SEQ ID NO: |
|---|---|---|---|---|---|---|
| egl_A | egl9_s | egl11_as | ALKO4245 | 0.6 | pALK2698 | 3 |
| egl_B | egl9_s | egl11_as | ALKO4245 | 0.4 | pALK2699 | 4 |

The deduced amino acid sequences from both of these PCR fragments had similarity to the published EG/Cel7B sequences (BLAST program, version 2.2.9 at NCBI, National Center for Biotechnology Information).

Acremonium thermophilum ALKO4245 genomic DNA was digested with several restriction enzymes for Southern blot analysis. The probes for the hybridization were the 566 bp (SEQ ID NO: 3 for gene egl_A) and 431 bp (SEQ ID NO: 4 for gene egl_B) EcoRI fragments, cut from the plasmids pALK2698 and pALK2699, respectively. The above probes were labeled by using digoxigenin according to supplier's instructions (Roche, Germany). Hybridizations were performed over night at 65° C. After hybridization the filters were washed 2×5 min at RT using 2×SSC-0.1% SDS followed by 2×15 min at 65° C. using 0.1×SSC-0.1% SDS. The *E. coli* strains RF8831 including the plasmid pALK2698, and RF8832 including the plasmid pALK2699, were deposited to the DSM collection under the accession numbers DSM 25490 and DSM 25491, respectively.

From the genomic DNA of *Acremonium thermophilum* ALKO4245, approximate 6.6 kb HindIII-digested fragment was hybridized using dioxigenin-labeled 566 bp EcoRI fragment from the pALK2698 as a probe. Correspondingly, about 9.5 kb EcoRI-digested fragment was hybridized with dioxigenin-labeled 431 bp EcoRI fragment of the pALK2699 also from the genomic DNA of the *Acremonium thermophilum* ALKO4245. The hybridizing genomic DNA fragments were isolated from the pool of the digested genomic fragments based on their size. The genomic fragments were isolated from agarose gel and were cloned into pBluescript II KS+ (Stratagene, USA) vectors cleaved with either HindIII (gene A) or EcoRI (gene B). Ligation mixtures were transformed into *Escherichia coli* XL 10-Gold cells (Stratagene) and plated on LB (Luria-Bertani) plates containing 50-100 µg/ml ampicillin. The *E. coli* colonies were screened for positive clones using colonial hybridization with the pALK2698 and pALK2699 inserts as probes in the hybridization conditions correspondingly to that described above for Southern blot analyses. Several positive clones were collected from the plates. They were shown by restriction digestion to contain inserts of expected sizes. The full-length gene encoding the *Acremonium thermophilum* ALKO4245 EG_A (egl_A, SEQ ID NO: 5) was sequenced from the 6.6 kb HindIII insert and the plasmid containing this insert was named pALK3152. The *E. coli* strain RF8939 including the plasmid pALK3152 was deposited to the DSM collection under the accession number DSM 25492. The gene encoding the *Acremonium thermophilum* ALKO4245 protein A was named as egl_A. Correspondingly, the full-length gene encoding the another *Acremonium thermophilum* ALKO4245 EG_B (egl_B. SEQ ID NO: 6) was sequenced from the 9.5 kb EcoRI insert and the plasmid containing this insert was named pALK3153. The *E. coli* strain RF8974 including the plasmid pALK3153 was deposited to the DSM collection under the accession number DSM 25493. The gene encoding the *Acremonium thermophilum* ALKO4245 protein B was named as egl_B. The relevant information on the genes and the deduced protein sequences (SEQ ID NOs: 5-8) are summarized in Table 5 and Table 6, respectively.

TABLE 5

The summary on the egl genes isolated from *Acremonium thermophilum* ALKO4245

| Gene | Length with introns (bp) [a] | Coding region (bp) [b] | No of putative introns | Lengths of putative introns (bp) | SEQ ID NO: |
|---|---|---|---|---|---|
| egl_A | 1520 | 1437 | 1 | 80 | 5 |
| egl_B | 1206 | 1203 | 0 | 0 | 6 |

[a] The STOP codon is included.
[b] The STOP codon is not included.

TABLE 6

The summary of the amino acid sequences deduced from the egl genes sequences from *Acremonium thermophilum* ALKO4245

| EG protein | No of aas | Length of SS [a] | CBM [b] | Predicted MW (Da), ss not incl [c] | Predicted pI, ss not incl | SEQ ID NO: |
|---|---|---|---|---|---|---|
| EG_A | 479 | 18 | S434 to L479 | 48010 | 4.26 | 7 |
| EG_B | 401 | 24 | — | 39063 | 4.80 | 8 |

[a] The prediction on the signal sequence was made using the program SignalP v3.0, NN/HMM (Nielsen et al., 1997; Nielsen & Krogh, 1998; Bendtsen et al., 2004).
[b] The cellulose-binding module (CBM) and linker region, the amino acids of the linker-CBM region are indicated [M1 (Met #1) included in numbering].
[c] The predicted signal sequence was not included. The prediction was made using Clone Manager version 9 for Windows, Sci-Ed Software The comparison of the deduced EG sequences from *Acremonium thermophilum* ALKO4245 to the databases are shown in Table 7.

TABLE 7

The highest identity sequences to the deduced EG_A and EG_B amino acid sequences from *Acremonium thermophilum* ALKO4245. The full-length amino acid sequences including the signal sequences were aligned. The database searches were performed at http://www.ebi.ac.uk/Tools/sss/fasta/ and http://www.ebi.ac.uktools/psa/emboss_needle/ using FASTA (EMBL-EBI, FASTA - Protein Similarity Search, UniProt Knowledgebase + NR Patent Proteins Level-1, BLOSUM50, Gap open −10, Gap extend −2), and EMBOSS Needle (EMBL-EBI, EMBOSS-Needle Pairwise Sequence Alignment, BLOSUM50, Gap open 10, Gap extend 0.5) for determining the degree of identity.

| Organism and accession number | Identity (%) |
|---|---|
| EG_A | 100 |
| *Podospora anserina*, XP_001906344.1 | 56.1 |
| EG_B | 100 |
| *Chaetomium globosum*, EAQ91517.1 | 57.6 |
| EG_A + EGI-CBM | 100 |
| *Podospora anserina*, XP_001906344.1 | 53.3 |
| EG_B + EGI-CBM | 100 |
| *Trichoderma reesei*, EGR48251.1 | 63.3 |
| EG_A + CBHI-CBM | 100 |
| *Podospora anserina*, XP_001906344.1 | 54.2 |
| EG_B + CBHI-CBM | 100 |
| *Thielavia terrestris*, XP_003653757.1 | 63.0 |

Example 2

Production of Recombinant EG/Cel7 Proteins in *Trichoderma reesei*

Expression plasmids were constructed for production of recombinant EG/Cel7 (EG_A and EG_B) proteins from *Acremonium thermophilum* ALKO4245 in *Trichoderma reesei*. The expression plasmids constructed are listed in Table 8. The recombinant cel7/egl genes (egl_A and egl_B), including their own signal sequences, were fused to the *T. reesei* cel7A/cbh1 promoter by PCR. The transcription termination was ensured by the *T. reesei* cel7A/cbh1 terminator and the *A. nidulans* amdS marker gene was used for selection of the transformants as described in Paloheimo et al. (2003). The linear expression cassettes (FIG. 1) were isolated from the vector backbones after NotI digestions and were transformed into *T. reesei* protoplasts. The host strain used does not produce any of the four major *T. reesei* cellulases (CBHI, CBHII, EGI, EGII). The transformations were performed as in Penttilä et al. (1987) with the modifications described in Karhunen et al. (1993), selecting acetamide as a sole nitrogen source (amdS marker gene). The transformants were purified on selection plates through single conidia prior to sporulating them on PD.

TABLE 8

The expression cassettes constructed to produce EG_A and EG_B recombinant proteins from *Acremonium thermophilum* ALKO4245 in *Trichoderma reesei*. The overall structure of the expression cassettes was as described in FIG. 1.

| Endoglucanase (Cel7) protein | Expression plasmid | Expression cassette [a] |
|---|---|---|
| EG_A | pALK3156 | 6.9 kb NotI |
| EG_B | pALK3157 | 6.5 kb NotI |

[a] The expression cassette for *T. reesei* transformation was isolated from the vector backbone by using NotI digestion.

The EG/Cel7 production of the transformants was analyzed from the culture supernatants of the shake flask cultivations. The transformants were inoculated from the PD slants to shake flasks containing 50 ml of complex lactose-based cellulase inducing medium (Joutsjoki et al. 1993) buffered with 5% $KH_2PO_4$. The EG/Cel7 protein production of the transformants was analyzed from the culture supernatants after growing them for 7 days at 30° C., 250 rpm. Heterologous production of recombinant proteins was analyzed by SDS-PAGE with subsequent Coomassie staining. The genotypes of the chosen transformants were confirmed by using Southern blot analyses in which several genomic digests were included and the respective expression cassette was used as a probe.

The best producing transformants were chosen to be cultivated in laboratory scale bioreactors. The transformants were cultivated in lab bioreactors at 28° C. in cellulase inducing complex medium 3-4 days with pH control 4.2±0.2 ($NH_3$/$H_3PO_4$) to obtain material for the application tests. The supernatants were recovered by centrifugation and filtering through EK filters (Pall SeitzSchenk Filtersystems GmbH, Bad Kreuznach, Germany).

Example 3

Production of the Recombinant *Acremonium thermophilum* ALKO4245 EG+*Trichoderma reesei* CBM Fusion Proteins in *T. reesei*

The atypical linker and CBM regions of *Acremonium thermophilum* ALKO4245 EG/Cel7_A (EG_A) were removed and the core region of the protein was fused to linker and CBM of *Trichoderma reesei* EGI/Cel7B (=EGI-CBM). *Acremonium thermophilum* ALKO4245 EG_B was also fused to linker and CBM of *Trichoderma reesei* EGI/Cel7B. For that purpose, the coding sequence of the core regions of EG_A and EG_B and the coding sequence of the linker and the CBM of *Trichoderma reesei* EGI/Cel7B were synthesized by PCR using following primers:
SEQ ID NO: 9 (forward sequence for EG_A core primer)
SEQ ID NO: 10 (reverse sequence for EG_A core primer)
SEQ ID NO: 11 (forward sequence of EGI-CBM primer)
SEQ ID NO: 12 (reverse sequence of EGI-CBM primer)
SEQ ID NO: 13 (forward sequence of EG_B primer)
SEQ ID NO: 14 (reverse sequence of EG_B primer)
SEQ ID NO: 15 (forward sequence of EGI-CBM primer)
SEQ ID NO: 16 (reverse sequence of EGI-CBM primer).

The PCR reaction mixture for synthesizing the DNA sequence encoding for EG_A core contained 1× Phusion HF Reaction Buffer (Finnzymes, Finland), 7.5 mM $MgCl_2$, 0.2 mM dNTPs, 1 µM of each primer, 3% DMSO, 4 units of Phusion DNA Polymerase (Finnzymes, Finland), and approximately 50 ng/200 µl of template DNA, containing full-length egl_A gene from *Acremonium thermophilum* ALKO4245. The conditions for the PCR reaction were the following: 30 sec initial denaturation at 98° C., followed by 24 cycles of 10 sec at 98° C., 30 sec annealing at 52.5° C. (±7.5° C. gradient), 30 sec extension at 72° C. and final extension at 72° C. for 7 min. The specific DNA fragment in PCR reaction was obtained at annealing temperature range from 45° C. to 60° C. The compatible restriction sites were created to the synthesized core fragment of *Acremonium thermophilum* ALKO4245 egl_A for the fusion to *Trichoderma reesei* cel7/egl1 linker-CBM region and ligation to expression vector.

The PCR reaction mixtures for synthesizing the DNA sequences encoding for EG_B and EGI-CBMs contained 1×F-511 Buffer for Dynazyme DNA Polymerase (Finnzymes, Finland), 0.2 mM dNTP Mix (Fermentas, Finland), 1 µM each primer, 3% DMSO (Finnzymes, Finland) 2-4 units of F-501L Dynazyme II DNA Polymerase (Finnzymes, Finland) and approximately 50 ng/200 µl of template DNA, containing the full-length egl_B gene from *Acremonium thermophilum* ALKO4245 and the full-length cel7/egl1 gene from *Trichoderma reesei*. The conditions for the PCR reactions were the following: 5 min initial denaturation at 95° C., followed by 28 cycles of 1 min at 95° C., 30 sec annealing at 52.5° C. (±7.5° C. gradient), 30 sec extension at 72° C. and a final extension at 72° C. for 5 min. The specific DNA fragments in PCR reactions were obtained at annealing temperature range from 45° C. to 60° C. The fragments created by primer combinations described above were then digested with compatible restriction enzymes and ligated together. The fragments amplified by PCR, primer combinations and compatible restriction enzymes are described in Table 9.

TABLE 9

PCR fragments amplified from *Acremonium thermophilum* ALKO4245 egl_A and egl_B and from *Trichoderma reesei* egl1 full length genes

| Fragment | Primer pairs | Restriction sites at the 5'- and 3'- ends | Length (bp) | SEQ ID NO: |
|---|---|---|---|---|
| egl_A core | SEQ ID NO: 9 + 10 | SacII + BsmBI | 1330 | 17 |
| egl_B core | SEQ ID NO: 13 + 14 | BamHI + SacI | 1272 | 18 |
| egl1-CBM | SEQ ID NO: 11 + 12 | BsmBI + XhoI | 281 | 19 |
| egl1-CBM | SEQ ID NO: 15 + 16 | SacI + AgeI | 212 | 20 |

The newly created fragments were then further ligated into expression vectors. The PCR amplified fragments in the expression plasmids were confirmed by sequencing (SEQ ID NO: 17 for egl_A core, SEQ ID NO: 18 for egl_B core, SEQ ID NO: 19 for egl1-CBM, SEQ ID NO: 20 for egl1-CBM, SEQ ID NO: 21 for egl_A+egl1-CBM and SEQ ID NO: 23 for EG_A+EGI-CBM, SEQ ID NO: 22 for egl_B+egl1-CBM and SEQ ID NO: 24 for EG_B+EGI-CBM). The fusion genes were also further cloned into pBluescript II KS+ vector for the patent deposition to DSM collection under following accession numbers: DSM 25657=*E. coli* strain RF10076 including the plasmid pALK3179 which contains the fusion gene egl_A+egl1-CBM. DSM 25658=*E. coli* strain RF10077 including the plasmid pALK3180 which contains the fusion gene egl_B+egl1-CBM.

*Acremonium thermophilum* ALKO4245 EG_A and EG_B were also fused to linker and CBM of *Trichoderma reesei* CBHI/Cel7A (=CBHI-CBM). The egl+cbh1-CBM fusion genes were designed such a way that the atypical linker and CBM regions of *Acremonium thermophilum* ALKO4245 egl_A would be removed and the remaining core region will be fused to linker and CBM region of *Trichoderma reesei* cel7A/cbh1 (=cbh1-CBM). *Trichoderma reesei* cel7A/cbh1 linker and CBM regions will be fused straight to *Acremonium thermophilum* cel7/egl_B, since it did not contain natural CBM. The fusion genes were ordered as synthetic constructs (from GenScript, USA). The synthetic fusion genes in plasmids were confirmed by sequencing (SEQ ID NO: 25 for egl_A+cbh1-CBM, SEQ ID NO: 26 for egl_B+cbh1-CBM, SEQ ID NO: 27 for EG_A+CBHI-CBM and SEQ ID NO: 28 for EG_B+CBHI-CBM). The *E. coli* strains RF9587 including the plasmid pALK3167, which contains the fusion gene egl_A+cbh1-CBM in pUC57, and RF9588 including the plasmid pALK3168 which contains the fusion gene egl_B+ cbh1-CBM in pUC57, were deposited to the DSM collection under the accession numbers DSM 25655 and DSM 25656, respectively.

The expression plasmids were constructed for production of recombinant EG+EGI-CBM (EG_A+EGI-CBM and EG_B+EGI-CBM) and EG+CBHI-CBM (EG_A+CBHI-CBM and EG_B+CBHI-CBM) fusion proteins (SEQ ID NO: 23-24 and 27-28 corresponding nucleic acid SEQ ID NO: 21-22 and 25-26). The expression plasmids constructed are listed in Table 10. The constructed egl_A+egl1-CBM, egl_B+ egl1-CBM, egl_A+cbh1-CBM and egl_B+cbh1-CBM fusion genes were fused to the *T. reesei* cbh1 (cel7A) promoter in the expression vector. The transcription termination was ensured by the *T. reesei* cel7A terminator and *A. nidulans* amdS marker gene was used for selection of the transformants as described in Paloheimo et al. (2003). The linear expression cassettes (FIG. 1) were isolated from the vector backbones after NotI digestions and were transformed into *T. reesei* protoplasts. The host strain used does not produce any of the four major *T. reesei* cellulases (CBHI, CBHII, EGI, EGII). The transformations were performed as in Penttilä et al. (1987) with the modifications described in Karhunen et al. (1993), selecting acetamide as a sole nitrogen source (amdS marker gene). The transformants were purified on selection plates through single conidia prior to sporulating them on PD.

TABLE 10

The expression cassettes constructed to produce EG + CBM fusion proteins in *Trichoderma reesei*. The overall structure of the expression cassettes was as described in FIG. 1.

| Fusion protein | Expression plasmid | Expression cassette [a] |
|---|---|---|
| EG_A + EGI-CBM | pALK3158 | 6.9 NotI |
| EG_B + EGI-CBM | pALK3159 | 6.7 NotI |
| EG_A + CBHI-CBM | pALK3161 | 6.9 NotI |
| EG_B + CBHI-CBM | pALK3162 | 6.7 NotI |

[a] The expression cassette for *T. reesei* transformation was isolated from the vector backbone by using NotI digestion.

The EG+CBM fusion protein production of the transformants was analyzed from the culture supernatant of the shake flask cultivations. The transformants were inoculated from the PD slants to shake flasks containing 50 ml of complex lactose-based cellulase inducing medium Joutsjoki et al. 1993) buffered with 5% $KH_2PO_4$. The EG+CBM fusion protein production of the transformants was analyzed from the culture supernatants after growing them for 7 days at 30° C., 250 rpm. Heterologous production of recombinant proteins was analyzed by SDS-PAGE with subsequent Coomassie staining. The genotypes of the chosen transformants were confirmed by using Southern blot analyses in which several genomic digests were included and the respective expression cassette was used as a probe.

The best producing transformants were chosen to be cultivated in laboratory scale bioreactors. The transformants were cultivated in lab bioreactors at 28° C. in cellulase inducing complex medium 3-4 days with pH control 4.2±0.2 ($NH_3$/$H_3PO_4$) to obtain material for the application tests. The supernatants were recovered by centrifugation and filtering through EK filters (Pall SeitzSchenk Filtersystems GmbH, Bad Kreuznach, Germany).

Example 4

Hydrolysis of Corn Fibre Substrate with Enzyme Preparations Comprising a Recombinant EG/Cel7 and EG/Cel7+CBM Endoglucanases Steam exploded corn fibre was suspended in 0.05 M sodium citrate buffer, pH 4.8. The final weight of the hydrolysis mixture was 1 g of which the total solids concentration was either 5% (w/w) or 17% (w/w). The substrate was hydrolyzed using different enzyme mixtures at a dosage of 0.5 mg of protein per g of total solids in 2 ml reaction tubes. The protein contents of the enzyme components were determined using the Pierce BCA assay kit (Thermo Scientific) with Bovine Serum Albumin (Thermo Scientific) as standard. The reaction tubes were agitated in a linear-shaking water bath 1086 from GFL, adjusted in different temperatures. For each sample point, a sample of 0.5 ml was taken from duplicate reaction tubes, and centrifuged, the supernatant was boiled for 20 minutes to terminate the enzymatic hydrolysis, and analyzed for reaction products from the hydrolysis. Seven separate mixture combinations were prepared (a basis mixture MIXTURE 1, MIXTURE 1_EG_A and MIXTURE 1_EG_B, MIXTURE 1_EG_A+EGI-CBM, MIXTURE 1_EG_B+ EGI-CBM, MIXTURE 1_EG_A+CBHI-CBM and MIXTURE 1_EG_B+CBHI-CBM) with different EG/Cel7 replacements.

A basis mixture of different cellulases was prepared using the following components:

Mesophilic EGI/Cel7B preparation containing recombinant *Trichoderma reesei* EGI/Cel7B.

CBHI/Cel7A preparation containing recombinant *Acremonium thermophilum* ALKO4245 CBHI/Cel7A (WO2007071818).

CBHII/Cel6A preparation containing recombinant *Acremonium thermophilum* ALKO4245 CBHII/Cel6A (WO2011080317).

EGII/Cel5A preparation containing recombinant *Thermoascus aurantiacus* ALKO4242 EGII/Cel5A (WO2007071818) with genetically attached CBM of *Trichoderma reesei* EGII/Cel5A.

β-glucosidase preparation containing *Acremonium thermophilum* ALKO4245 β-glucosidase/Cel3A (WO2007071818).

Xylanase preparation containing *Thermoascus aurantiacus* ALKO4242 Xyn10A xylanase (WO2007071818).

All cellulases were heterologously produced as monocomponents in *Trichoderma reesei* host strain having cellulasefree background (the genes encoding the four major cellulases CBHI/Cel7A, CBHII/Cel6A, EGI/Cel7B and EGII/Cel5A were deleted). Crude culture supernatants were used in the mixture. The enzyme components were combined as follows to prepare a basis mixture: cellobiohydrolase CBHI/Cel7A preparation 60%, cellobiohydrolase CBHII/Cel6A preparation 15%, endoglucanase EGII/Cel5A preparation 10%, endoglucanase EGI/Cel7B preparation 8%, β-glucosidase βG/Cel3A preparation 4% and xylanase Xyn10A preparation 3%. This enzyme mixture was designated as MIXTURE 1.

For testing EG endoglucanase performance in the hydrolysis with MIXTURE 1, 8% of the EGI/Cel7B endoglucanase component of MIXTURE 1 was replaced by:

EG/Cel7 preparation containing recombinant *Acremonium thermophilum* ALKO4245 EG_A or EG/Cel7 preparation containing recombinant *Acremonium thermophilum* ALKO4245 EG_B. The mixtures containing *Acremonium thermophilum* ALKO4245 EG/Cel7 proteins EG_A or EG_B were designated as MIXTURE 1_EG_A and MIXTURE 1_EG_B, respectively.

For testing EG+CBM fusion protein performance in the hydrolysis with MIXTURE 1, 8% of the EGI/Cel7B endoglucanase component of MIXTURE 1 was replaced by:

EG+CBM preparation containing recombinant *Acremonium thermophilum* ALKO4245 EG_A genetically fused to *Trichoderma reesei* EGI-CBM (EG_A+EGI-CBM) or EG+CBM preparation containing recombinant *Acremonium thermophilum* ALKO4245 EG_B genetically fused to *Trichoderma reesei* EGI-CBM (EG_B+EGI-CBM) or EG+CBM preparation containing recombinant *Acremonium thermophilum* ALKO4245 EG_A genetically fused to *Trichoderma reesei* CBHI-CBM (EG_A+CBHI-CBM) or EG+CBM preparation containing recombinant *Acremonium thermophilum* ALKO4245 EG_B genetically fused to *Trichoderma reesei* CBHI-CBM (EG_B+CBHI-CBM).

The mixtures containing the fusion proteins EG_A+EGI-CBM, EG_B+EGI-CBM, EG_A+CBHI-CBM or EG_B+CBHI-CBM were designated as MIXTURE 1_EG_A+EGI-CBM, MIXTURE 1_EG_B+EGI-CBM, MIXTURE 1_EG_A+CBHI-CBM and MIXTURE 1_EG_B+CBHI-CBM, respectively.

For all the mixtures the hydrolysis was performed at 37° C. and 55° C. Samples were taken from the hydrolysis after 48 h, quantified by HPLC and the concentration of glucose was determined (FIG. 2).

Figure 2A:
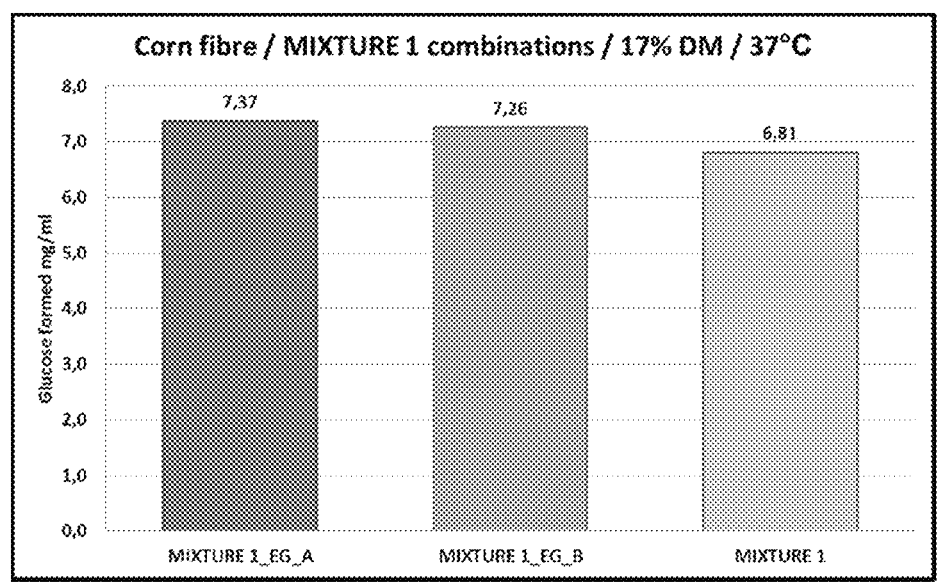
FIGS. 2A-2B show results from hydrolysis of steam exploded corn fibre performed with enzyme mixtures comprising the EG/Cel7 endoglucanases of the invention. The corn fibre substrate was hydrolyzed using different enzyme mixtures at a dosage of 0.5 mg of protein per g of total solids all at 37° C. and 55° C. in high dry matter conditions. The compositions of the enzyme mixtures; basis enzyme mixture (MIXTURE 1) and compositions comprising the EG_A and EG_B, are described in more detail in Example 5. Samples from five different tubes were taken after 48 hours hydrolysis time and quantified by HPLC, in which the concentration of glucose was determined. The concentration of glucose is presented.
Figure 2B:
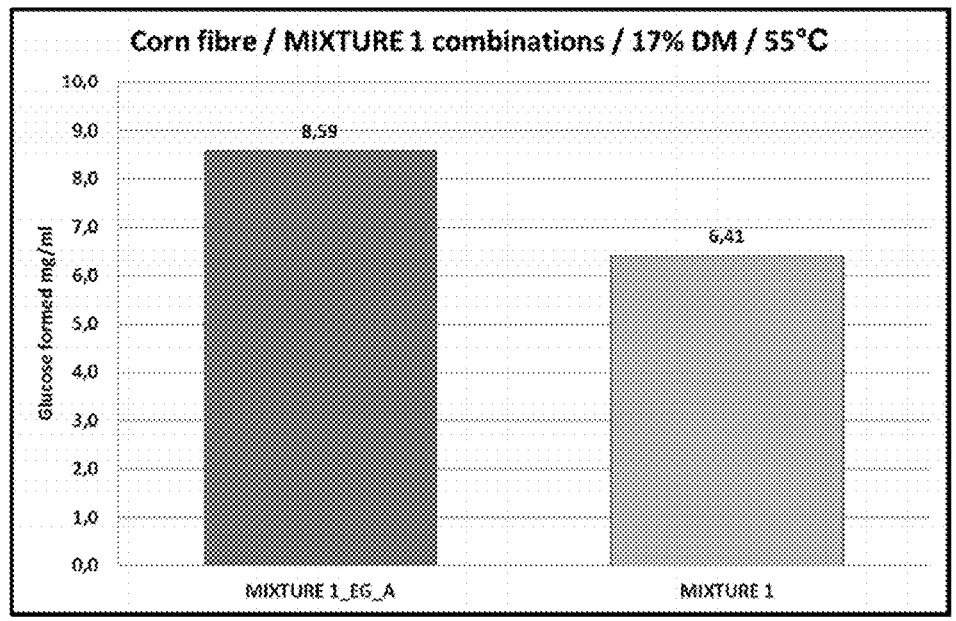

The results show better performance of the MIXTURE 1_EG_A and MIXTURE 1_EG_B at 37° C. with high (17%) dry matter content. The amount of glucose released from corn fibre substrate was found to increase 9% for the MIXTURE 1_EG_A and 7% for the MIXTURE 1_EG_B compared to the MIXTURE 1 (FIG. 2A). At 55° C. and with high dry matter content MIXTURE 1_EG_A was found to increase glucose yield 34% compared to the enzyme mix MIXTURE 1 (FIG. 2B).

Figure 3A:
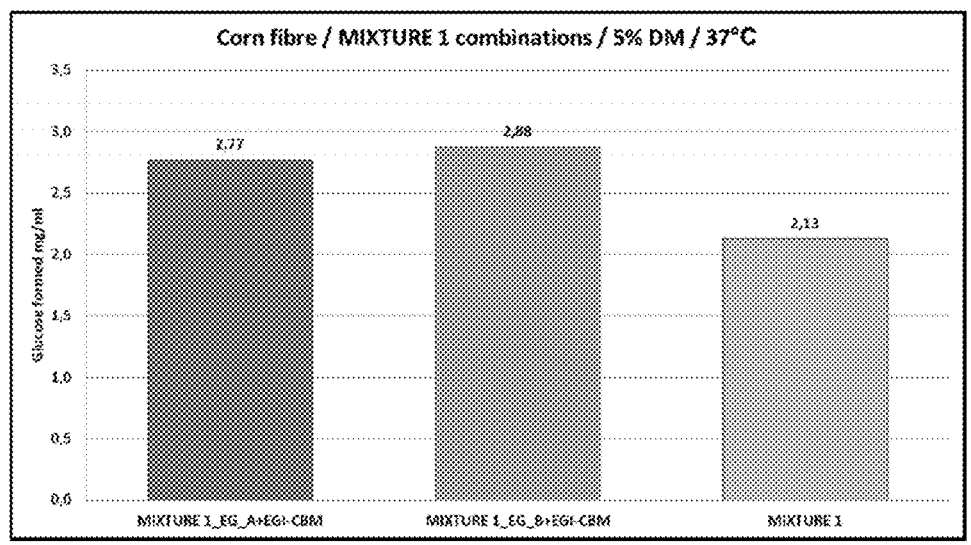
FIGS. 3A-3C show results from hydrolysis of steam exploded corn fibre performed with enzyme mixtures comprising the EG_A+EGI-CBM and EG_B+EGI-CBM fusion protein of the invention. The corn fibre substrate was hydrolyzed using different enzyme mixtures at a dosage of 0.5 mg of protein per g of total solids all at 37° C. with both low and high dry matter conditions and at 55° C. with high dry matter conditions. The compositions of the enzyme mixtures, a basis enzyme mixture (MIXTURE 1) and compositions comprising the EG_A+EGI-CBM and EG_B+EGI-CBM, are described in more detail in Example 5. Samples from five different tubes were taken after 48 hours hydrolysis time and quantified by HPLC, in which the concentration of glucose was determined. The concentration of glucose is presented.
Figure 3B:
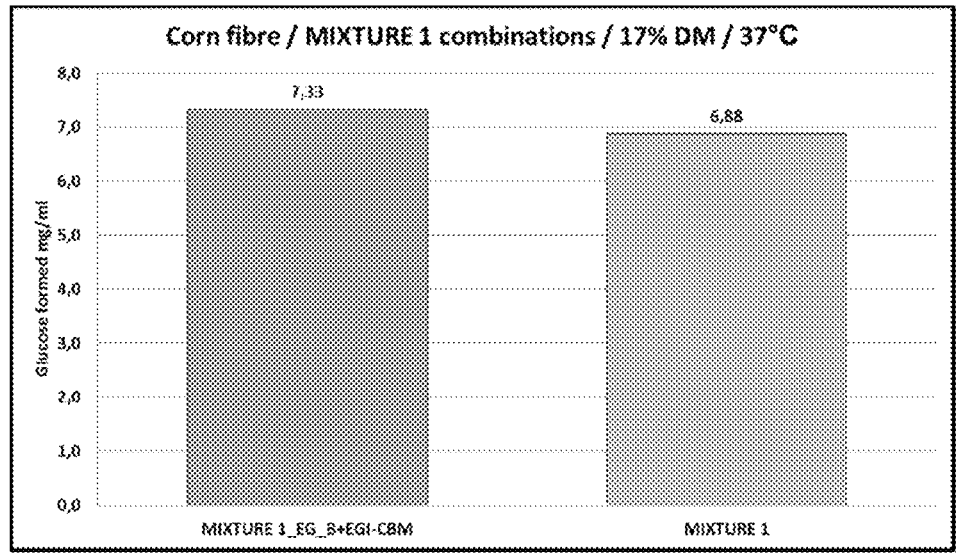
Figure 3C:
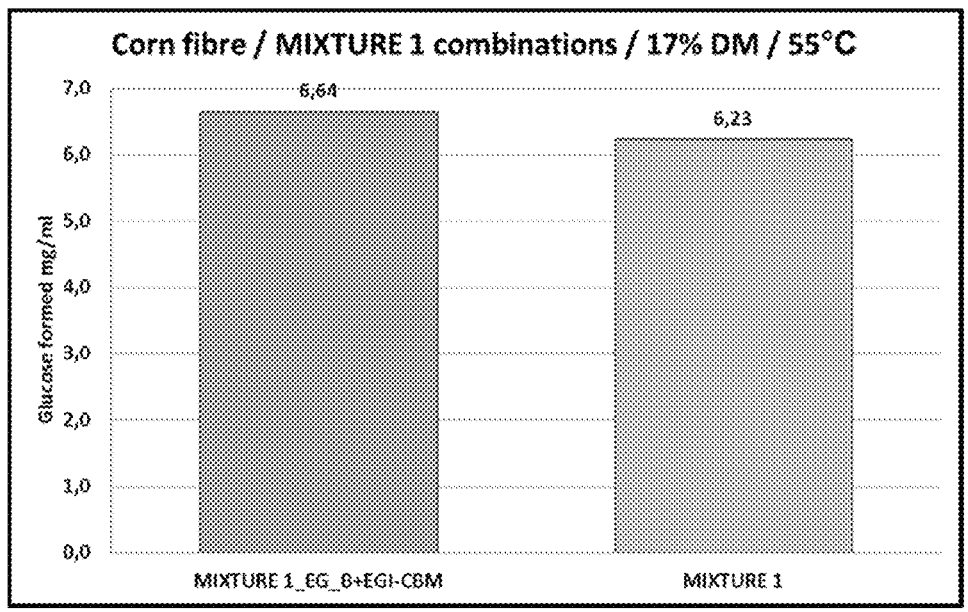

For the EG+EGI-CBM (EG_A+EGI-CBM and EG_B+EGI-CBM) fusion proteins the results show better performance of the MIXTURE 1_EG_A+EGI-CBM and MIXTURE 1_EG_B+EGI-CBM at 37° C. in low (5%) dry matter conditions. The amount of glucose released from corn fibre substrate was found to increase 30% for the MIXTURE 1_EG_A+EGI-CBM and 35% for the MIXTURE 1_EG_B+EGI-CBM compared to the MIXTURE 1 (FIG. 3A). In high dry matter conditions MIXTURE 1_EG_B+EGI-CBM mix was found to increase glucose yield 7% at both temperatures 37° C. and 55° C. compared to the enzyme mix MIXTURE 1 (FIGS. 3B and 3C).

Figure 4A:
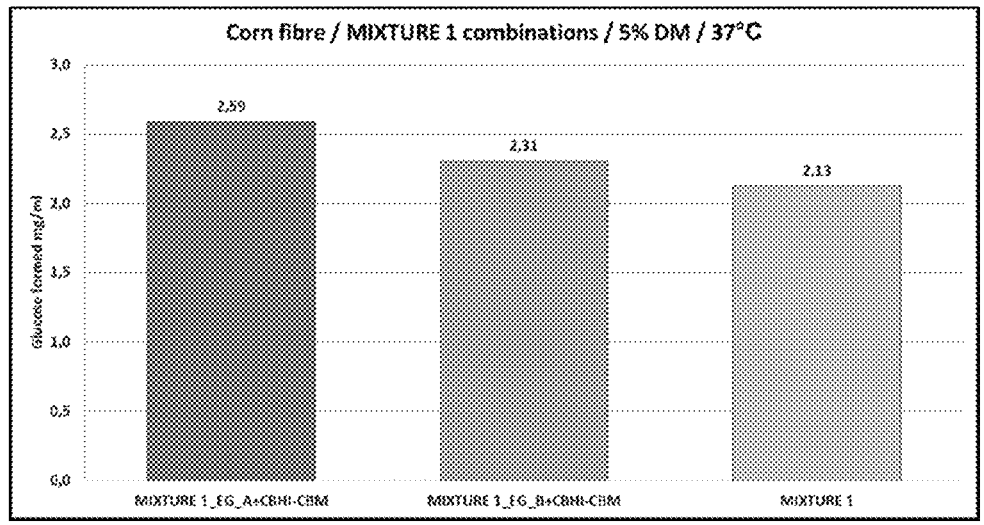
FIGS. 4A-4C show results from hydrolysis of steam exploded corn fibre performed with enzyme mixtures comprising the EG_A+CBHI-CBM and EG_B+CBHI-CBM fusion protein of the invention. The corn fibre substrate was hydrolyzed using different enzyme mixtures at a dosage of 0.5 mg of protein per g of total solids all at 37° C. with both low and high dry matter conditions and at 55° C. with high dry matter conditions. The compositions of the enzyme mixtures; a basis enzyme mixture (MIXTURE 1) and compositions comprising the EG_A+CBHI-CBM and EG_B+CBHI-CBM, are described in more detail in Example 5. Samples from five different tubes were taken after 48 hours hydrolysis time and quantified by HPLC, in which the concentration of glucose was determined. The concentration of glucose is presented.
Figure 4B:
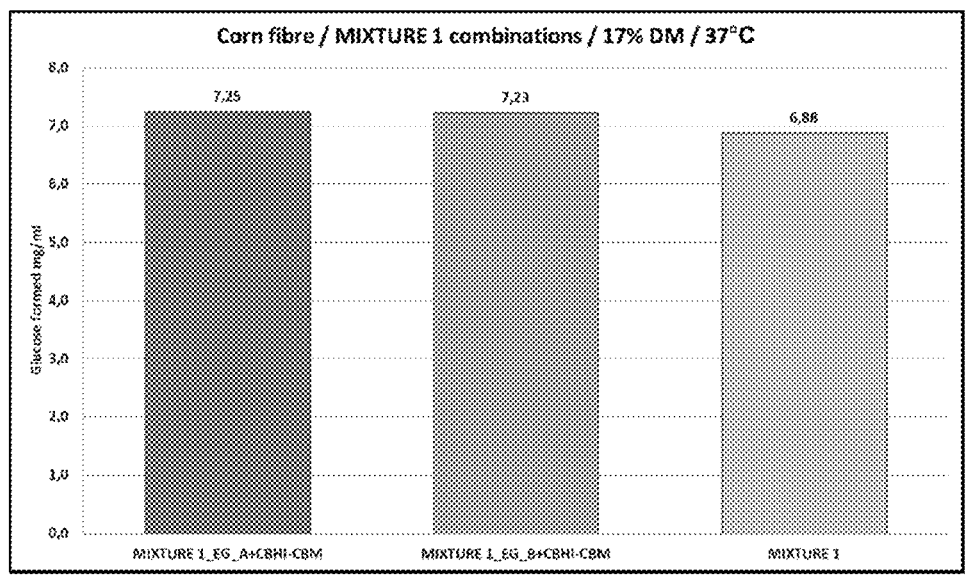
Figure 4C:
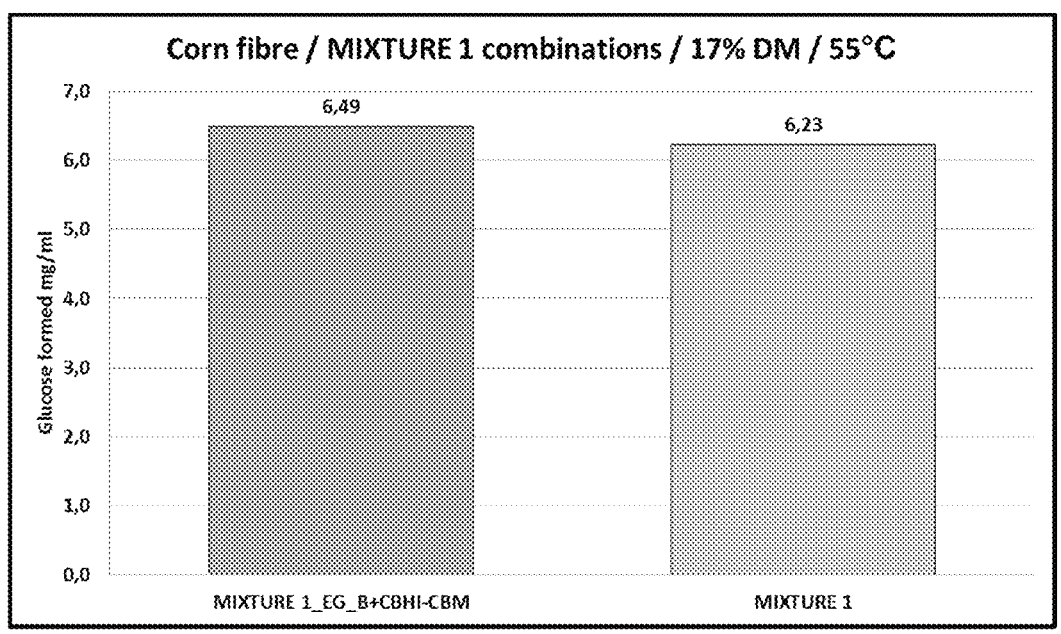

For the EG+CBHI-CBM (EG_A+CBHI-CBM and EG_B+CBHI-CBM) fusion proteins the results show better performance of the MIXTURE 1_EG_A+CBHI-CBM and MIXTURE 1_EG_B+CBHI-CBM at 37° C. in both low and high dry matter conditions. The amount of glucose released from corn fibre substrate was found to increase 22% in low dry matter conditions and 5% in high dry matter conditions for the MIXTURE 1_EG_A+CBHI-CBM, and 8% in low dry matter conditions and 5% in high dry matter conditions for the MIXTURE 1_EG_B+CBHI-CBM compared to the MIXTURE 1 (FIGS. 4A and 4B). In high dry matter conditions at 55° C. MIXTURE 1_EG_B+CBHI-CBM was found to increase glucose yield 4% compared to the MIXTURE 1 (FIG. 4C).

REFERENCES

Badger, P. C. (2002) Ethanol from cellulose: a general review. In Trends in new crops and new uses. J. Janick and A. Whipkey (eds.). ASHS Press, Alexandria, Va., USA, pp. 17-21.

Bailey M., Siika-aho M., Valkeajärvi A. and Penttilä M. (1993) Hydrolytic properties of two cellulases of *Trichoderma reesei* expressed in yeast. Biotehnol. Appl. Biochem 17: 65-76

Bendtsen J. D., Nielsen H., von Heijne G. and Brunak S. (2004) Improved prediction of signal peptides: SignalP 3.0. J. Mol. Biol. 340: 783-795.

Coen, D. M. (2001) The polymerase chain reaction. In: Ausubel, F. M., Brent, R., Kingston, R. E., More, D. D., Seidman, J. G., Smith, K. and Struhl, K. (eds.) Current protocols in molecular biology. John Wiley & Sons. Inc., Hoboken, USA.

Gellissen, G. (ed.) (2005) Production of recombinant proteins. Novel microbial and eukaryotic expression systems. Wiley-VCH Verlag Gmbh&Co. Weinheim, Germany.

Haakana H., Miettinen-Oinonen A., Joutsjoki V., Mäntylä A., Suominen P, and Vehmaanperä J. (2004) Cloning of cellulase genes from *Melanocarpus albomyces* and their efficient expression in *Trichoderma reesei*. Enz. Microbiol. Technol. 34: 159-167.

Henrissat B. (1991) A classification of glycosyl hydrolases based on amino acid sequence similarities. Biochem. J. 280: 309-316.

Henrissat B. and Bairoch A. (1993) New families in the classification of glycosyl hydrolases based on amino acid sequence similarities. Biochem. J. 293: 781-788.

Henrissat B. and Bairoch A. (1996). Updating the sequence-based classification of glycosyl hydrolases. Biochem. J. 316: 695-696

Hong J., H. Tamaki, K. Yamamoto, and Kumagai H. (2003a) Cloning of a gene encoding a thermo-stabile endo-β-1,4-glucanase from *Thermoascus aurantiacus* and its expression in yeast. Biotech. Letters 25: 657-661.

Hong J., Tamaki H., Yamamoto K. and Kumagai H. (2003b) Cloning of a gene encoding thermostable cellobiohydrolase from *Thermoascus aurantiacus* and its expression in yeast. Appl. Microbiol. Biotechnol. 63: 42-50.

Joutsjoki, V. V., Torkkeli T. K. and Nevalainen K. M. H. (1993) Transformation of *Trichoderma reesei* with the Hormoconis resinae glucoamylase P (gamP) gene: production of a heterologous glucoamylase by *Trichoderma reesei*. Curr. Genet. 24: 223-228.

Karhunen T., Mäntylä A., Nevalainen K. M. H. and Suominen P. L. (1993) High frequency one-step gene replacement in *Trichoderma reesei*. I. Endoglucanase I overproduction. Mol. Gen. Genet. 241: 515-522.

Miettinen-Oinonen A, J Londesborough, V Joutsjoki, R Lantto, J Vehmaanperä. 2004. Three cellulases from *Melanocarpus albomyces* with application in textile industry. Enzyme Microb. Technol. 34: 332-341.

Needleman S. and Wunsch C. (1970) A general method applicable to the search for similarities in the amino acid sequence of two proteins. Journal of Molecular Biology 48, 443-453.

Nielsen H., Engelbrecht J., Brunak S. and von Heijne G. (1997) Identification of prokaryotic and eykaryotic signal peptides and prediction of their cleavage sites. Protein Engineering 10: 1-6.

Nielsen H and A Krogh. 1998. Prediction of signal peptides and signal anchors by a hidden Markov model. In: Proceedings of the Sixth international Conference of Intelligent Systems for Molecular Biology (ISMB 6), AAAI Press, Menlo Park, Calif., pp. 122-130.

Paloheimo M., Mäntylä A., Kallio J., and Suominen P. (2003) High-yield production of a bacterial xylanase in the filamentous fungus *Trichoderma reesei* requires a carrier polypeptide with an intact domain structure. Appl. Env. Microbiol. 69: 7073-7082.

Penttilä M., Nevalainen H., Rättö M., Salminen E. and Knowles J. (1987) A versatile transformation system for the cellulolytic filamentous fungus *Trichoderma reesei*. Gene 61:155-164.

Raeder U. and Broda P. (1985) Rapid preparation of DNA from filamentous fungi. Lett. Appl. Microbiol. 1: 17-20.

Sambrook J., Fritsch E. F. and Maniatis T. (1989) Molecular cloning, a laboratory manual. Cold Spring Harbor Laboratory, New York, US.

Sambrook J. and Russell D. W. (2001) Molecular cloning, a laboratory manual. Cold Spring Harbor Laboratory, New York, US.

Tuohy M., Walsh J., Murray P., Claeyssens M., Cuffe M., Savage A. and Coughan M. (2002) Kinetic parameters and mode of action of cellobiohydrolases produced by *Talaromyces emersonii*. Biochem. Biophys. Acta 1596: 366-380 (abstract).

Visser H., Joosten V., Punt P. J., Gusakov A. V., Olson P. T., Joosten R., Bartels J., Visser J., Sinitsyn A. P., Emalfarb M. A., Verdoes J. C. and Wery J. (2011) Development of a mature fungal technology and production platform for industrial enzymes based on a *Myceliophthora thermophila* isolate, previously known as *Chrysosporium lucknowense* C1. Industrial Biotechnology. June 7(3): 214-223.

Voutilainen S., Puranen T., Siika-aho, M., Lappalainen A., Alapuranen M., and Kallio J., (2008) Cloning, expression, and characterization of novel thermostable family 7 cellobiohydrolases. Biotechnology and Bioengineering Vol. 101 Nr. 3, 515-528.

Van Tilbeurgh, H., Loonties, F., de Bruyne, C. and Claeyssens, M. (1988) Fluorogenic and chromogenic glycosides as substrates and ligands of carbohydrases. Methods Enzymol. 160:45-59.

The invention claimed is:

1. A recombinant fusion protein having endoglucanase activity and comprising an amino acid sequence having at least about 95% sequence identity to an amino acid sequence of SEQ ID NO: 23 or SEQ ID NO: 27.

2. The fusion protein of claim 1, which comprises an endoglucanase domain which originates from *Acremonium thermophilum*.

3. The fusion protein of claim 1, comprising a cellulose binding module (CBM) of *Tricoderma reesei*.

4. The fusion protein of claim 3, wherein said CBM is a CBM derived from *T. reesei* endoglucanase I ("EGI/Cel7B") or *T. reesei* cellobiohydrolase I ("CBHI/Cel7A").

5. The fusion protein of claim 3, wherein the fusion protein comprises an amino acid sequence having SEQ ID NO: 23 or SEQ ID NO: 27.

6. An enzyme preparation in the form of spent culture medium comprising an amino acid sequence having at least about 95% sequence identity to endoglucanase A ("EG_A") having SEQ ID NO: 7, or endoglucanase fusion protein having SEQ ID NO: 23 or SEQ ID NO: 27 and at least one further enzyme selected from the group consisting of cellobiohydrolase, endoglucanase, beta-glucosidase, beta-glucanase, xyloglucanase, xylanase, beta-xylosidase, mannanase, beta-mannosidase, α-glucuronidase, acetyl xylan esterase, α-arabinofuranosidase, α-galactosidase, pectinase, endo- or exo-α-L-arabinases, endo- and exo-galactoronase, endopectinlyase, pectate lyase, pectinesterase, phenol esterase, ligninase, lignin peroxidase, manganese-dependent peroxidase, $H_2O_2$-generating enzyme and laccase with or without a mediator.

7. The enzyme preparation of claim 6 comprising cellobiohydrolase CBHI/Cel 7A, cellobiohydrolase CBHII/Cel6A, endoglucanase EGII/Cel5A, beta-glucosidase βG/Cel3A, xylanase Xyn10A and endoglucanase EG_A.

8. The enzyme preparation of claim 6 comprising cellobiohydrolase CBHI/Cel 7A, cellobiohydrolase CBHII/Cel6A, endoglucanase EGII/Cel5A, beta-glucosidase βG/Cel3A, xylanase Xyn10A and endoglucanase fusion protein comprising an amino acid sequence having SEQ ID NO: 23 or SEQ ID NO: 27.

9. A method for treating cellulosic material with a fusion protein of claim 1 or an enzyme preparation of claim 6, wherein the method comprises the following steps:
    i) reacting the cellulosic material with said fusion protein or the enzyme preparation, and
    ii) obtaining at least partially hydrolyzed cellulosic material.

10. The method of claim 9 wherein the at least partially hydrolyzed cellulosic material is obtained in processing biofuel, biomass, starch, textile, detergent, pulp and paper, food, feed or beverages.

11. The fusion protein of claim 1, which comprises an endoglucanase domain which originates from *A. thermophilum* CBS 116240.

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgytgyaayg aratggayat                                            20

<210> SEQ ID NO 2
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t

<400> SEQUENCE: 2
swrtcnarcc arttcat                                               17

<210> SEQ ID NO 3
<211> LENGTH: 566
<212> TYPE: DNA
<213> ORGANISM: Acremonium thermophilum

<400> SEQUENCE: 3
aattcgccct tgtatcgagc cagttcatga agtcgcccgc cgagttccag atgctgaaga      60
cgagtaccat gccgcgctcc agcgaggcgc ccatgccatc catgcctccc aggcggaggt     120
actgcgaggc attggcggcg gtgcagaagg cttgcgtcac ggatccgccg ctggcgtcgt     180
```

```
tcacgttggg cgacgtagag tcgagctggt tcgtgttcga ggggacgggc tcgttctgga    240
tgaccttgcc gtcctggacg tacaggcgac ggatctcggc gagcgtcccc gaaccggtag    300
aggcattgcc agagtcggtc aaaaactgag tcaccaccgt gaagggtttg gtggtgtcca    360
cggtcttgcc ggggccgtaa aagtctttga ggcccgcgcg gaatgggttg acgccgcaac    420
cgtcgtggtc gcatacgccg gcgtcggtct tgccacactc gtcgccagag cacaagaagg    480
agcccacgcc gctgcaggta tgaggcgtca tggcggtagc catggcattt gcttcccaga    540
tgtccatctc attgcagcaa agggcg                                          566

<210> SEQ ID NO 4
<211> LENGTH: 431
<212> TYPE: DNA
<213> ORGANISM: Acremonium thermophilum

<400> SEQUENCE: 4
aattcgccct ttgctgcaat gagatggaca tcctggaggc caactcgcag gccaacgcct     60
tcaccccgca cccctgcagg aacggcaact gcgacaagag cggctgcggc tacaaccccc    120
acgccaaggg cttccgcaac tactggggcc ccggtatgac cgtcgacacg tccaagccct    180
tcaccatcac cacccagttc gtcgagagtg gcgggtccct cagccagatc gtgcgcaggt    240
acgcccaggg cgggcggccg atccccagcg cggcgtcggg cggcgacgtc atccaggcca    300
gcgcctgcgg cacggcgcag agcttcgcg ggctggccga gatgggcgcg cgctggaccc    360
gcggcatggt cctcgtcttc agcatctgga acgacccggc ccagaacatg aactggctcg    420
actgaagggc g                                                          431

<210> SEQ ID NO 5
<211> LENGTH: 1520
<212> TYPE: DNA
<213> ORGANISM: Acremonium thermophilum

<400> SEQUENCE: 5
atggctttca gactggcagc tgcgctgcct ttccttcttc tcctggcaca cgcacaaaag     60
attggcactg cggttcccga ggtccatccg aagctggtga cccagacctg caccacttcg    120
ggaggttgtg ttgaccgcca acattgctc gtgacggatg ccctctcgcg tccgttccac    180
aaggttggag atccttcggt gccgtgcacg ccgttgaaca ccaccctctg cccggacgcc    240
gccacttgtg cggcaaactg cgagctcgaa ggggtggagt atggtagcct cggcgtgctt    300
accgccggcc gagctgtcac tctgcggcag tacctcttcg atggcgacgc cttcacctct    360
gtcagcccgc gcctctacct gctggccgag gacggcatga actatgagct gctcaagctg    420
aacggccaag agctctccta tgacgtcgac gtgtcgcagc tgggctgcgg catgaatggc    480
gccttgtacc tctccgagat ggacgcctcg gggtctagga gcgacctgaa cccagcaggt    540
gcccagtatg gcacgggcta ctgcgatgcg cagtgcttta tgtgtcgtt tatcaacgga    600 ctggtatgtg tcgtggaat tgaacgtatc cgtcatagcc aagtcaaaca tgaactaact    660
cttcacacat cttcctccga cagccgaatc tcaacaactc gggtgcctgc tgcaacgaga    720
tggatatctg ggaagcaaat gccatggcta ccgccatgac gcctcatacc tgcagcggcg    780
tgggctcctt cttgtgctct ggcgacgagt gtggcaagac cgacgccggc gtatgcgacc    840
acgacggttg cggcgtcaac ccattccgcg cgggcctcaa agacttctac ggccccggca    900
agaccgtgga caccaccaaa ccccttcacg tggtgactca gttttttgacc gactctggca    960 atgcctctac cggttcgggg acgctcgccg agatccgtcg cctgtacgtc caggacggca    1020
```

| | |
|---|---|
| aggtcatcca gaacgagccc gtccctcga acacgaacca gctcgactct acgtcgccca | 1080 |
| acgtgaacga cgccagcggc ggatccgtga cgcaagcctt ctgcaccgcc gccaatgcct | 1140 |
| cgcagtacct ccgcctggga ggcatggatg gcatgggcgc ctcgctggag cgcggcatgg | 1200 |
| tactcgtctt cagcatctgg aactcggcgg gcgacttcat gaactggctg acagcggcg | 1260 |
| aggccggccc gtgcagcaac acctccgcg acccggcccg catcgtggcc gagacgcccg | 1320 |
| aagtctccgt caccttctcc aacatccgct ggggagatat tgggtccacc ttcaacgcct | 1380 |
| cgtcttcgcc gctgcgcaac gggacgaatg ccgctttctt gagctcgaat gcgaagagcg | 1440 |
| gtacggcgcc gcacactgct gctgcgtctg taggtgtctg ggccatgcta ccgcagtct | 1500 |
| ccgcttatct ccttctctga | 1520 |

<210> SEQ ID NO 6
<211> LENGTH: 1206
<212> TYPE: DNA
<213> ORGANISM: Acremonium thermophilum

<400> SEQUENCE: 6

| | |
|---|---|
| atggcgcgcc agactcattc ctacggcatc ttggccgtcg cccttgtctt ctggcgccag | 60 |
| ctggctcacg ctcagaaccc agccgcgccc gaggtgcatc cgtcgctgcc cacctggaag | 120 |
| tgcaccacgg cgggcggttg cgtgcagcag aacacgtccg tcgtgctcga ctgggacgcg | 180 |
| cgcgccatcg tgccgtctgg cggcggcggc ggcggcggtg gcgggtcctg caagacggcc | 240 |
| accggcggcg tcagtgccag cctctgtccc gacgaggcca cctgcgccaa gaactgcgtc | 300 |
| gtccagccca tcgccaacta cacggagcac ggcgtgtcca ccgcgggcga cgccctgacc | 360 |
| ctgtaccact acgtgcgcat caacggccag ctgtcggccc agtcgccccg cgtctacctg | 420 |
| ctgggccccg acgcgactac cgagatgctg cacctcctgg ccgcgagct cagcttcgac | 480 |
| gtcgacctgt ccacgctgcc ctgcggcgag aacggcgccc tctacctctc cgagatgagc | 540 |
| gccggcggcg ggcgcaaccc cgacaacacg ggcggcgcga gctacggctc gggctactgc | 600 |
| gacgcccagt gccccaccct ggcgtggcgc aacggcacca tcaacaccgg ccgccagggc | 660 |
| tactgctgcg acgagatgga catcctggag gccaactcgc aggccaacgc cttcacccg | 720 |
| caccctgca ggaacggcaa ctgcgacaag agcggctgcg gctacaaccc ctacgccaag | 780 |
| ggcttccgca actactgggg ccccggtatg accgtcgaca cgtccaagcc cttcaccatc | 840 |
| accacccagt tcgtcgagag tggcgggtcc ctcagccaga tcgtgcgcag gtacgccag | 900 |
| ggcgggcggc cgatccccag cgcggcgtcg ggcggcgacg tcatccaggc cagcgcctgc | 960 |
| ggcacggcgc agagcttcgg cgggctggcc gagatgggcg cggcgctgga ccgcggcatg | 1020 |
| gtcctcgtct tcagcatctg gaacgacccg gcccagaaca tgaactggct cgacagcggc | 1080 |
| accgcggggc cctgcagcag cgcggcgggc agtccggcca cgatccaggc gcagcatccg | 1140 |
| gatacgcacg ttgtcttctc gaacatccgc tggggcgaca ttggctcgac gacccagacg | 1200 |
| tcgtag | 1206 |

<210> SEQ ID NO 7
<211> LENGTH: 479
<212> TYPE: PRT
<213> ORGANISM: Acremonium thermophilum

```
<400> SEQUENCE: 7

Met Ala Phe Arg Leu Ala Ala Leu Pro Phe Leu Leu Leu Leu Ala
1               5                   10                  15

His Ala Gln Lys Ile Gly Thr Ala Val Pro Glu Val His Pro Lys Leu
            20                  25                  30

Val Thr Gln Thr Cys Thr Thr Ser Gly Gly Cys Val Asp Arg Gln Thr
                35                  40                  45

Leu Leu Val Thr Asp Ala Leu Ser Arg Pro Phe His Lys Val Gly Asp
        50                  55                  60

Pro Ser Val Pro Cys Thr Pro Leu Asn Thr Thr Leu Cys Pro Asp Ala
65                  70                  75                  80

Ala Thr Cys Ala Ala Asn Cys Glu Leu Glu Gly Val Glu Tyr Gly Ser
                85                  90                  95

Leu Gly Val Leu Thr Ala Gly Arg Ala Val Thr Leu Arg Gln Tyr Leu
            100                 105                 110

Phe Asp Gly Asp Ala Phe Thr Ser Val Ser Pro Arg Leu Tyr Leu Leu
            115                 120                 125

Ala Glu Asp Gly Met Asn Tyr Glu Leu Leu Lys Leu Asn Gly Gln Glu
    130                 135                 140

Leu Ser Tyr Asp Val Asp Val Ser Gln Leu Gly Cys Gly Met Asn Gly
145                 150                 155                 160

Ala Leu Tyr Leu Ser Glu Met Asp Ala Ser Gly Ser Arg Ser Asp Leu
                165                 170                 175

Asn Pro Ala Gly Ala Gln Tyr Gly Thr Gly Tyr Cys Asp Ala Gln Cys
            180                 185                 190

Phe Asn Val Ser Phe Ile Asn Gly Leu Pro Asn Leu Asn Asn Ser Gly
        195                 200                 205

Ala Cys Cys Asn Glu Met Asp Ile Trp Glu Ala Asn Ala Met Ala Thr
    210                 215                 220

Ala Met Thr Pro His Thr Cys Ser Gly Val Gly Ser Phe Leu Cys Ser
225                 230                 235                 240

Gly Asp Glu Cys Gly Lys Thr Asp Ala Gly Val Cys Asp His Asp Gly
                245                 250                 255

Cys Gly Val Asn Pro Phe Arg Ala Gly Leu Lys Asp Phe Tyr Gly Pro
            260                 265                 270

Gly Lys Thr Val Asp Thr Thr Lys Pro Phe Thr Val Thr Gln Phe
        275                 280                 285

Leu Thr Asp Ser Gly Asn Ala Ser Thr Gly Ser Gly Thr Leu Ala Glu
    290                 295                 300

Ile Arg Arg Leu Tyr Val Gln Asp Gly Lys Val Ile Gln Asn Glu Pro
305                 310                 315                 320

Val Pro Ser Asn Thr Asn Gln Leu Asp Ser Thr Ser Pro Asn Val Asn
                325                 330                 335

Asp Ala Ser Gly Gly Ser Val Thr Gln Ala Phe Cys Thr Ala Ala Asn
            340                 345                 350

Ala Ser Gln Tyr Leu Arg Leu Gly Gly Met Asp Gly Met Gly Ala Ser
        355                 360                 365

Leu Glu Arg Gly Met Val Leu Val Phe Ser Ile Trp Asn Ser Ala Gly
    370                 375                 380

Asp Phe Met Asn Trp Leu Asp Ser Gly Glu Ala Gly Pro Cys Ser Asn
385                 390                 395                 400

Thr Ser Gly Asp Pro Ala Arg Ile Val Ala Glu Thr Pro Glu Val Ser
                405                 410                 415
```

```
Val Thr Phe Ser Asn Ile Arg Trp Gly Asp Ile Gly Ser Thr Phe Asn
            420                 425                 430

Ala Ser Ser Ser Pro Leu Arg Asn Gly Thr Asn Ala Ala Phe Leu Ser
            435                 440                 445

Ser Asn Ala Lys Ser Gly Thr Ala Pro His Thr Ala Ala Ala Ser Val
    450                 455                 460

Gly Val Trp Ala Met Leu Ala Ala Val Ser Ala Tyr Leu Leu Leu
465                 470                 475

<210> SEQ ID NO 8
<211> LENGTH: 401
<212> TYPE: PRT
<213> ORGANISM: Acremonium thermophilum

<400> SEQUENCE: 8

Met Ala Arg Gln Thr His Ser Tyr Gly Ile Leu Ala Val Ala Leu Val
1               5                   10                  15

Phe Trp Arg Gln Leu Ala His Ala Gln Asn Pro Ala Ala Pro Glu Val
            20                  25                  30

His Pro Ser Leu Pro Thr Trp Lys Cys Thr Thr Ala Gly Gly Cys Val
            35                  40                  45

Gln Gln Asn Thr Ser Val Val Leu Asp Trp Asp Ala Arg Ala Ile Val
    50                  55                  60

Pro Ser Gly Gly Gly Gly Gly Gly Gly Ser Cys Lys Thr Ala
65                  70                  75                  80

Thr Gly Gly Val Ser Ala Ser Leu Cys Pro Asp Glu Ala Thr Cys Ala
                85                  90                  95

Lys Asn Cys Val Val Gln Pro Ile Ala Asn Tyr Thr Glu His Gly Val
            100                 105                 110

Ser Thr Ala Gly Asp Ala Leu Thr Leu Tyr His Tyr Val Arg Ile Asn
            115                 120                 125

Gly Gln Leu Ser Ala Gln Ser Pro Arg Val Tyr Leu Leu Gly Pro Asp
    130                 135                 140

Gly Asp Tyr Glu Met Leu His Leu Leu Gly Arg Glu Leu Ser Phe Asp
145                 150                 155                 160

Val Asp Leu Ser Thr Leu Pro Cys Gly Glu Asn Gly Ala Leu Tyr Leu
                165                 170                 175

Ser Glu Met Ser Ala Gly Gly Gly Arg Asn Pro Asp Asn Thr Gly Gly
            180                 185                 190

Ala Ser Tyr Gly Ser Gly Tyr Cys Asp Ala Gln Cys Pro Thr Leu Ala
            195                 200                 205

Trp Arg Asn Gly Thr Ile Asn Thr Gly Arg Gln Gly Tyr Cys Cys Asp
    210                 215                 220

Glu Met Asp Ile Leu Glu Ala Asn Ser Gln Ala Asn Ala Phe Thr Pro
225                 230                 235                 240

His Pro Cys Arg Asn Gly Asn Cys Asp Lys Ser Gly Cys Gly Tyr Asn
                245                 250                 255

Pro Tyr Ala Lys Gly Phe Arg Asn Tyr Trp Gly Pro Gly Met Thr Val
            260                 265                 270

Asp Thr Ser Lys Pro Phe Thr Ile Thr Thr Gln Phe Val Glu Ser Gly
            275                 280                 285

Gly Ser Leu Ser Gln Ile Val Arg Arg Tyr Ala Gln Gly Gly Arg Pro
    290                 295                 300

Ile Pro Ser Ala Ala Ser Gly Gly Asp Val Ile Gln Ala Ser Ala Cys
305                 310                 315                 320
```

```
Gly Thr Ala Gln Ser Phe Gly Gly Leu Ala Glu Met Gly Ala Ala Leu
                325                 330                 335

Asp Arg Gly Met Val Leu Val Phe Ser Ile Trp Asn Asp Pro Ala Gln
            340                 345                 350

Asn Met Asn Trp Leu Asp Ser Gly Thr Ala Gly Pro Cys Ser Ser Ala
        355                 360                 365

Ala Gly Ser Pro Ala Thr Ile Gln Ala Gln His Pro Asp Thr His Val
    370                 375                 380

Val Phe Ser Asn Ile Arg Trp Gly Asp Ile Gly Ser Thr Thr Gln Thr
385                 390                 395                 400

Ser
```

<210> SEQ ID NO 9
<211> LENGTH: 50
<212> TYPE: DNA
<213> ORGANISM: Artificial Sequence
<220> FEATURE:
<223> OTHER INFORMATION: primer

<400> SEQUENCE: 9
cgagccgcgg atggctttca gactggcagc tgcgctgcct ttccttcttc        50

<210> SEQ ID NO 10
<211> LENGTH: 40
<212> TYPE: DNA
<213> ORGANISM: artificial sequence
<220> FEATURE:
<223> OTHER INFORMATION: primer

<400> SEQUENCE: 10
cgggcgtctc ggccacgatg cgggccgggt cgccggaggt        40

<210> SEQ ID NO 11
<211> LENGTH: 120
<212> TYPE: DNA
<213> ORGANISM: Artificial Sequence
<220> FEATURE:
<223> OTHER INFORMATION: primer

<400> SEQUENCE: 11
catcgtggcc gagacgcccg aagtctccgt caccttctcc aacatccgct ggggagatat        60
tgggtccacc ttcaacgccg cgccccgcc cccgcctgcg tccagcacga cgttttcgac        120

<210> SEQ ID NO 12
<211> LENGTH: 51
<212> TYPE: DNA
<213> ORGANISM: Artificial Sequence
<220> FEATURE:
<223> OTHER INFORMATION: primer

<400> SEQUENCE: 12
cgtcctcgag ctaaaggcat tgcgagtagt agtcgttgct atactggcac g        51

<210> SEQ ID NO 13
<211> LENGTH: 50
<212> TYPE: DNA
<213> ORGANISM: Artificial Sequence
<220> FEATURE:
<223> OTHER INFORMATION: primer

<400> SEQUENCE: 13
cgagggatcc atggcgcgcc agactcattc ctacggcatc ttggccgtcg        50

<210> SEQ ID NO 14
<211> LENGTH: 95
<212> TYPE: DNA
<213> ORGANISM: Artificial Sequence
<220> FEATURE:
<223> OTHER INFORMATION: primer

<400> SEQUENCE: 14

| | |
|---|---|
| gtcgagctcc tccgtgtagt cgaaaacgtc gtgctggacg caggcggggg cggggggcgcc | 60 |
| gacgtctggg tcgtcgagcc aatgtcgccc cagcg | 95 |

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15

| | |
|---|---|
| gaggagctcg acgacttcga gcagcccgag ctgcacgcag | 40 |

<210> SEQ ID NO 16
<211> LENGTH: 55
<212> TYPE: DNA
<213> ORGANISM: Artificial Sequence
<220> FEATURE:
<223> OTHER INFORMATION: primer

<400> SEQUENCE: 16

| | |
|---|---|
| ctcgaccggt ctaaaggcat tgcgagtagt agtcgttgct atactggcac gtagt | 55 |

<210> SEQ ID NO 17
<211> LENGTH: 1330
<212> TYPE: DNA
<213> ORGANISM: Acremonium thermophilum

<400> SEQUENCE: 17

| | |
|---|---|
| cgagccgcgg atggctttca gactggcagc tgcgctgcct ttccttcttc tcctggcaca | 60 |
| cgcacaaaag attggcactg cggttcccga ggtccatccg aagctggtga cccagacctg | 120 |
| caccacttcg ggaggttgtg ttgaccgcca acattgctc gtgacggatg ccctctcgcg | 180 |
| tccgttccac aaggttggag atccttcggt gccgtgcacg ccgttgaaca ccaccctctg | 240 |
| cccggacgcc gccacttgtg cggcaaactg cgagctcgaa ggggtggagt atggtagcct | 300 |
| cggcgtgctt accgccggcc gagctgtcac tctgcggcag tacctcttcg atggcgacgc | 360 |
| cttcacctct gtcagcccgc gcctctacct gctggccgag gacggcatga actatgagct | 420 |
| gctcaagctg aacggccaag agctctccta tgacgtcgac gtgtcgcagc tgggctgcgg | 480 |
| catgaatggc gccttgtacc tctccgagat ggacgcctcg ggtctagga gcgacctgaa | 540 |
| cccagcaggt gcccagtatg gcacgggcta ctgcgatgcg cagtgcttta atgtgtcgtt | 600 |
| tatcaacgga ctggtatgtg ctcgtggaat tgaacgtatc cgtcatagcc aagtcaaaca | 660 |
| tgaactaact cttcacacat cttcctccga cagccgaatc tcaacaactc gggtgcctgc | 720 |
| tgcaacgaga tggatatctg ggaagcaaat gccatggcta ccgccatgac gcctcatacc | 780 |
| tgcagcggcg tgggctccct cttgtgctct ggcgacgagt gtggcaagac cgacgccggc | 840 |
| gtatgcgacc acgacggttg cggcgtcaac ccattccgcg cgggcctcaa agacttctac | 900 |
| ggccccggca gaccgtggga caccaccaaa ccccttcacgg tggtgactca gttttttgacc | 960 |
| gactctggca atgcctctac cggttcgggg acgctcgccg agatccgtcg cctgtacgtc | 1020 |

-continued

| | |
|---|---|
| caggacggca aggtcatcca gaacgagccc gtccctcga acacgaacca gctcgactct | 1080 |
| acgtcgccca acgtgaacga cgccagcggc ggatccgtga cgcaagcctt ctgcaccgcc | 1140 |
| gccaatgcct cgcagtacct ccgcctggga ggcatggatg gcatgggcgc ctcgctggag | 1200 |
| cgcggcatgg tactcgtctt cagcatctgg aactcggcgg gcgacttcat gaactggctg | 1260 |
| gacagcggcg aggccggccc gtgcagcaac acctccggcg acccggcccg catcgtggcc | 1320 |
| gagacgcccg | 1330 |

<210> SEQ ID NO 18
<211> LENGTH: 1272
<212> TYPE: DNA
<213> ORGANISM: Acremonium thermophilum

<400> SEQUENCE: 18

| | |
|---|---|
| cgagggatcc atggcgcgcc agactcattc ctacggcatc ttggccgtcg cccttgtctt | 60 |
| ctggcgccag ctggctcacg ctcagaaccc agccgcgccc gaggtgcatc cgtcgctgcc | 120 |
| cacctggaag tgcaccacgg cgggcggttg cgtgcagcag aacacgtccg tcgtgctcga | 180 |
| ctgggacgcg cgcgccatcg tgccgtctgg cggcggcggc ggcggcggtg gcgggtcctg | 240 |
| caagacggcc accggcggcg tcagtgccag cctctgtccc gacgaggcca cctgcgccaa | 300 |
| gaactgcgtc gtccagccca tcgccaacta cggagcac ggcgtgtcca ccgcgggcga | 360 |
| cgccctgacc ctgtaccact acgtgcgcat caacggccag ctgtcggccc agtcgccccg | 420 |
| cgtctacctg ctgggccgg acggcgacta cgagatgctg cacctcctgg gccgcgagct | 480 |
| cagcttcgac gtcgacctgt ccacgctgcc ctgcggcgag aacggcgccc tctacctctc | 540 |
| cgagatgagc gccggcggcg gcgcaaccc cgacaacacg gcggcgcga gctacggctc | 600 |
| gggctactgc gacgcccagt gccccaccct ggcgtggcgc aacggcacca tcaacaccgg | 660 |
| ccgccagggc tactgctgcg acgagatgga catcctggag gccaactcgc aggccaacgc | 720 |
| cttcacccg caccctgca ggaacggcaa ctgcgacaag agcggctgcg gctacaaccc | 780 |
| ctacgccaag ggcttccgca actactgggg ccccggtatg accgtcgaca cgtccaagcc | 840 |
| cttcaccatc accacccagt tcgtcgagag tggcgggtcc ctcagccaga tcgtgcgcag | 900 |
| gtacgcccag ggcggcggc cgatccccag cgcggcgtcg ggcggcgacg tcatccaggc | 960 |
| cagcgcctgc ggcacggcgc agagcttcgg cgggctggcc gagatgggcg cggcgctgga | 1020 |
| ccgcggcatg gtcctcgtct tcagcatctg gaacgacccg gcccagaaca tgaactggct | 1080 |
| cgacagcggc accgcggggc cctgcagcag cgcggcgggc agtccggcca cgatccaggc | 1140 |
| gcagcatccg gatacgcacg ttgtcttctc gaacatccgc tggggcgaca ttggctcgac | 1200 |
| gacccagacg tcggcgcccc cgcccccgcc tgcgtccagc acgacgtttt cgactacacg | 1260 |
| gaggagctcg ac | 1272 |

<210> SEQ ID NO 19
<211> LENGTH: 281
<212> TYPE: DNA
<213> ORGANISM: Trichoderma reesei

<400> SEQUENCE: 19

| | |
|---|---|
| catcgtggcc gagacgcccg aagtctccgt caccttctcc aacatccgct ggggagatat | 60 |
| tgggtccacc ttcaacgccg cgccccgcc ccgcctgcg tccagcacga cgttttcgac | 120 |
| tacacggagg agctcgacga cttcgagcag cccgagctgc acgcagactc actgggggca | 180 |

```
gtgcggtggc attgggtaca gcgggtgcaa gacgtgcacg tcgggcacta cgtgccagta      240
tagcaacgac tactactcgc aatgccttta gctcgaggac g                           281

<210> SEQ ID NO 20
<211> LENGTH: 212
<212> TYPE: DNA
<213> ORGANISM: Trichoderma reesei

<400> SEQUENCE: 20
gaggagctcg acgacttcga gcagcccgag ctgcacgcag actcactggg ggcagtgcgg       60
tggcattggg tacagcgggt gcaagacgtg cacgtcgggc actacgtgcc agtatagcaa      120
cgactgttcg tatccccatg cctgacggga gtgattttga gatgctaacc gctaaaatac      180
agactactcg caatgccttt agaccggtcg ag                                    212

<210> SEQ ID NO 21
<211> LENGTH: 1571
<212> TYPE: DNA
<213> ORGANISM: Acremonium thermophilum

<400> SEQUENCE: 21
atggctttca gactggcagc tgcgctgcct ttccttcttc tcctggcaca cgcacaaaag       60
attggcactg cggttcccga ggtccatccg aagctggtga cccagacctg caccacttcg      120
ggaggttgtg ttgaccgcca acattgctc gtgacggatg ccctctcgcg tccgttccac      180
aaggttggag atccttcggt gccgtgcacg ccgttgaaca ccaccctctg cccggacgcc      240
gccacttgtg cggcaaactg cgagctcgaa ggggtggagt atggtagcct cggcgtgctt      300
accgccggcc gagctgtcac tctgcggcag tacctcttcg atggcgacgc cttcacctct      360
gtcagcccgc gcctctacct gctggccgag gacggcatga actatgagct gctcaagctg      420
aacggccaag agctctccta tgacgtcgac gtgtcgcagc tgggctgcgg catgaatggc      480
gccttgtacc tctccgagat ggacgcctcg ggtctagga gcgacctgaa cccagcaggt      540
gcccagtatg gcacgggcta ctgcgatgcg cagtgcttta atgtgtcgtt tatcaacgga      600
ctggtatgtg tcgtggaat tgaacgtatc cgtcatagcc aagtcaaaca tgaactaact      660
cttcacacat cttcctccga cagccgaatc tcaacaactc gggtgcctgc tgcaacgaga      720
tggatatctg ggaagcaaat gccatggcta ccgccatgac gcctcatacc tgcagcggcg      780
tgggctcctt cttgtgctct ggcgacgagt gtggcaagac cgacgccggc gtatgcgacc      840
acgacggttg cggcgtcaac ccattccgcg cgggcctcaa agacttctac ggccccggca      900
agaccgtgga caccaccaaa cccttcacgg tggtgactca gttttttgacc gactctggca      960 atgcctctac cggttcgggg acgctcgccg agatccgtcg cctgtacgtc caggacggca     1020
aggtcatcca gaacgagccc gtccccctcga cacgaaccca gctcgactct acgtcgccca     1080
acgtgaacga cgccagcggc ggatccgtga cgcaagcctt ctgcaccgcc gccaatgcct     1140
cgcagtacct ccgcctggga ggcatggatg gcatgggcgc ctcgctggag cgcggcatgg     1200
tactcgtctt cagcatctgg aactcggcgg gcgacttcat gaactggctg gacagcggcg     1260
aggccggccc gtgcagcaac acctccggcg accggcccg catcgtggcc gagacgcccg     1320
aagtctccgt cacccttctcc aacatccgct ggggagatat tgggtccacc ttcaacgccg     1380 cgccccgcc cccgctgcg tccagcacga cgttttcgac tacacggagg agctcgacga     1440
cttcgagcag cccgagctgc acgcagactc actggggca gtgcggtggc attgggtaca     1500
```

```
                                     -continued gcgggtgcaa gacgtgcacg tcgggcacta cgtgccagta tagcaacgac tactactcgc    1560
aatgccttta g                                                         1571

<210> SEQ ID NO 22
<211> LENGTH: 1395
<212> TYPE: DNA
<213> ORGANISM: Acremonium thermophilum

<400> SEQUENCE: 22
atggcgcgcc agactcattc ctacggcatc ttggccgtcg cccttgtctt ctggcgccag      60
ctggctcacg ctcagaaccc agccgcgccc gaggtgcatc cgtcgctgcc cacctggaag     120
tgcaccacgg cgggcggttg cgtgcagcag aacacgtccg tcgtgctcga ctgggacgcg     180
cgcgccatcg tgccgtctgg cggcggcggc ggcggcggtg cgggtcctg caagacggcc      240 accggcggcg tcagtgccag cctctgtccc gacgaggcca cctgcgccaa gaactgcgtc     300
gtccagccca tcgccaacta cacggagcac ggcgtgtcca ccgcgggcga cgccctgacc     360
ctgtaccact acgtgcgcat caacggccag ctgtcggccc agtcgccccg cgtctacctg     420
ctgggcccgg acggcgacta cgagatgctg cacctcctgg ccgcgagct cagcttcgac      480 gtcgacctgt ccacgctgcc ctgcggcgag aacggcgccc tctacctctc cgagatgagc     540
gccggcggcg gcgcaaccc cgacaacacg ggcggcgcga gctacggctc gggctactgc      600
gacgcccagt gccccaccct ggcgtggcgc aacggcacca tcaacaccgg ccgccagggc     660
tactgctgcg acgagatgga catcctggag ccaactcgc aggccaacgc cttcaccccg      720
cacccctgca ggaacggcaa ctgcgacaag agcggctgcg gctacaaccc ctacgccaag     780
ggcttccgca actactgggg ccccggtatg accgtcgaca cgtccaagcc cttcaccatc     840
accacccagt tcgtcgagag tggcgggtcc ctcagccaga tcgtgcgcag gtacgcccag     900
ggcgggcggc cgatccccag cgcggcgtcg ggcggcgacg tcatccaggc cagcgcctgc     960
ggcacggcgc agagcttcgg cgggctgccc gagatgggcg cggcgctgga ccgcggcatg    1020
gtcctcgtct tcagcatctg gaacgacccg gcccagaaca tgaactggct cgacagcggc    1080 accgcgggc cctgcagcag cgcggcgggc agtccggcca cgatccaggc gcagcatccg    1140
gatacgcacg ttgtcttctc gaacatccgc tggggcgaca ttggctcgac gacccagacg    1200
tcggcgcccc cgccccgcc tgcgtccagc acgacgtttt cgactacacg gaggagctcg    1260
acgacttcga gcagcccgag ctgcacgcag actcactggg ggcagtgcgg tggcattggg    1320
tacagcgggt gcaagacgtg cacgtcgggc actacgtgcc agtatagcaa cgactactac    1380
tcgcaatgcc tttag                                                     1395

<210> SEQ ID NO 23
<211> LENGTH: 496
<212> TYPE: PRT
<213> ORGANISM: Acremonium thermophilum

<400> SEQUENCE: 23

Met Ala Phe Arg Leu Ala Ala Ala Leu Pro Phe Leu Leu Leu Leu Ala
1               5                   10                  15

His Ala Gln Lys Ile Gly Thr Ala Val Pro Glu Val His Pro Lys Leu
            20                  25                  30

Val Thr Gln Thr Cys Thr Thr Ser Gly Gly Cys Val Asp Arg Gln Thr
        35                  40                  45

Leu Leu Val Thr Asp Ala Leu Ser Arg Pro Phe His Lys Val Gly Asp
    50                  55                  60
```

```
Pro Ser Val Pro Cys Thr Pro Leu Asn Thr Thr Leu Cys Pro Asp Ala
 65                  70                  75                  80

Ala Thr Cys Ala Ala Asn Cys Glu Leu Glu Gly Val Glu Tyr Gly Ser
                 85                  90                  95

Leu Gly Val Leu Thr Ala Gly Arg Ala Val Thr Leu Arg Gln Tyr Leu
            100                 105                 110

Phe Asp Gly Asp Ala Phe Thr Ser Val Ser Pro Arg Leu Tyr Leu Leu
        115                 120                 125

Ala Glu Asp Gly Met Asn Tyr Glu Leu Leu Lys Leu Asn Gly Gln Glu
    130                 135                 140

Leu Ser Tyr Asp Val Asp Val Ser Gln Leu Gly Cys Gly Met Asn Gly
145                 150                 155                 160

Ala Leu Tyr Leu Ser Glu Met Asp Ala Ser Gly Ser Arg Ser Asp Leu
                165                 170                 175

Asn Pro Ala Gly Ala Gln Tyr Gly Thr Gly Tyr Cys Asp Ala Gln Cys
            180                 185                 190

Phe Asn Val Ser Phe Ile Asn Gly Leu Pro Asn Leu Asn Asn Ser Gly
        195                 200                 205

Ala Cys Cys Asn Glu Met Asp Ile Trp Glu Ala Asn Ala Met Ala Thr
    210                 215                 220

Ala Met Thr Pro His Thr Cys Ser Gly Val Gly Ser Phe Leu Cys Ser
225                 230                 235                 240

Gly Asp Glu Cys Gly Lys Thr Asp Ala Gly Val Cys Asp His Asp Gly
                245                 250                 255

Cys Gly Val Asn Pro Phe Arg Ala Gly Leu Lys Asp Phe Tyr Gly Pro
            260                 265                 270

Gly Lys Thr Val Asp Thr Thr Lys Pro Phe Thr Val Val Thr Gln Phe
        275                 280                 285

Leu Thr Asp Ser Gly Asn Ala Ser Thr Gly Ser Gly Thr Leu Ala Glu
    290                 295                 300

Ile Arg Arg Leu Tyr Val Gln Asp Gly Lys Val Ile Gln Asn Glu Pro
305                 310                 315                 320

Val Pro Ser Asn Thr Asn Gln Leu Asp Ser Thr Ser Pro Asn Val Asn
                325                 330                 335

Asp Ala Ser Gly Gly Ser Val Thr Gln Ala Phe Cys Thr Ala Ala Asn
            340                 345                 350

Ala Ser Gln Tyr Leu Arg Leu Gly Gly Met Asp Gly Met Gly Ala Ser
        355                 360                 365

Leu Glu Arg Gly Met Val Leu Val Phe Ser Ile Trp Asn Ser Ala Gly
    370                 375                 380

Asp Phe Met Asn Trp Leu Asp Ser Gly Glu Ala Gly Pro Cys Ser Asn
385                 390                 395                 400

Thr Ser Gly Asp Pro Ala Arg Ile Val Ala Glu Thr Pro Glu Val Ser
                405                 410                 415

Val Thr Phe Ser Asn Ile Arg Trp Gly Asp Ile Gly Ser Thr Phe Asn
            420                 425                 430

Ala Ala Pro Pro Pro Pro Ala Ser Ser Thr Thr Phe Ser Thr Thr
        435                 440                 445

Arg Arg Ser Ser Thr Thr Ser Ser Ser Pro Ser Cys Thr Gln Thr His
    450                 455                 460
```

-continued

Trp Gly Gln Cys Gly Gly Ile Gly Tyr Ser Gly Cys Lys Thr Cys Thr
465                 470                 475                 480

Ser Gly Thr Thr Cys Gln Tyr Ser Asn Asp Tyr Tyr Ser Gln Cys Leu
            485                 490                 495

<210> SEQ ID NO 24
<211> LENGTH: 464
<212> TYPE: PRT
<213> ORGANISM: Acremonium thermophilum

<400> SEQUENCE: 24

Met Ala Arg Gln Thr His Ser Tyr Gly Ile Leu Ala Val Ala Leu Val
1               5                   10                  15

Phe Trp Arg Gln Leu Ala His Ala Gln Asn Pro Ala Ala Pro Glu Val
            20                  25                  30

His Pro Ser Leu Pro Thr Trp Lys Cys Thr Thr Ala Gly Gly Cys Val
        35                  40                  45

Gln Gln Asn Thr Ser Val Val Leu Asp Trp Asp Ala Arg Ala Ile Val
50                  55                  60

Pro Ser Gly Gly Gly Gly Gly Gly Gly Ser Cys Lys Thr Ala
65                  70                  75                  80

Thr Gly Gly Val Ser Ala Ser Leu Cys Pro Asp Glu Ala Thr Cys Ala
                85                  90                  95

Lys Asn Cys Val Val Gln Pro Ile Ala Asn Tyr Thr Glu His Gly Val
            100                 105                 110

Ser Thr Ala Gly Asp Ala Leu Thr Leu Tyr His Tyr Val Arg Ile Asn
        115                 120                 125

Gly Gln Leu Ser Ala Gln Ser Pro Arg Val Tyr Leu Leu Gly Pro Asp
130                 135                 140

Gly Asp Tyr Glu Met Leu His Leu Leu Gly Arg Glu Leu Ser Phe Asp
145                 150                 155                 160

Val Asp Leu Ser Thr Leu Pro Cys Gly Glu Asn Gly Ala Leu Tyr Leu
                165                 170                 175

Ser Glu Met Ser Ala Gly Gly Arg Asn Pro Asp Asn Thr Gly Gly
            180                 185                 190

Ala Ser Tyr Gly Ser Gly Tyr Cys Asp Ala Gln Cys Pro Thr Leu Ala
        195                 200                 205

Trp Arg Asn Gly Thr Ile Asn Thr Gly Arg Gln Gly Tyr Cys Cys Asp
210                 215                 220

Glu Met Asp Ile Leu Glu Ala Asn Ser Gln Ala Asn Ala Phe Thr Pro
225                 230                 235                 240

His Pro Cys Arg Asn Gly Asn Cys Asp Lys Ser Gly Cys Gly Tyr Asn
                245                 250                 255

Pro Tyr Ala Lys Gly Phe Arg Asn Tyr Trp Gly Pro Gly Met Thr Val
            260                 265                 270

Asp Thr Ser Lys Pro Phe Thr Ile Thr Thr Gln Phe Val Glu Ser Gly
        275                 280                 285

Gly Ser Leu Ser Gln Ile Val Arg Arg Tyr Ala Gln Gly Gly Arg Pro
290                 295                 300

Ile Pro Ser Ala Ala Ser Gly Gly Asp Val Ile Gln Ala Ser Ala Cys
305                 310                 315                 320

Gly Thr Ala Gln Ser Phe Gly Gly Leu Ala Glu Met Gly Ala Ala Leu
                325                 330                 335

Asp Arg Gly Met Val Leu Val Phe Ser Ile Trp Asn Asp Pro Ala Gln
            340                 345                 350

```
Asn Met Asn Trp Leu Asp Ser Gly Thr Ala Gly Pro Cys Ser Ser Ala
            355                 360                 365

Ala Gly Ser Pro Ala Thr Ile Gln Ala Gln His Pro Asp Thr His Val
        370                 375                 380

Val Phe Ser Asn Ile Arg Trp Gly Asp Ile Gly Ser Thr Thr Gln Thr
385                 390                 395                 400

Ser Ala Pro Pro Pro Pro Ala Ser Ser Thr Thr Phe Ser Thr Thr
                405                 410                 415

Arg Arg Ser Ser Thr Thr Ser Ser Pro Ser Cys Thr Gln Thr His
            420                 425                 430

Trp Gly Gln Cys Gly Gly Ile Gly Tyr Ser Gly Cys Lys Thr Cys Thr
            435                 440                 445

Ser Gly Thr Thr Cys Gln Tyr Ser Asn Asp Tyr Tyr Ser Gln Cys Leu
        450                 455                 460

<210> SEQ ID NO 25
<211> LENGTH: 1568
<212> TYPE: DNA
<213> ORGANISM: Acremonium thermophilum

<400> SEQUENCE: 25
```

| | | | | | |
|---|---|---|---|---|---|
| atggctttca | gactggcagc | tgcgctgcct | tccttcttc | tcctggcaca | cgcacaaaag | 60 |
| attggcactg | cggttccga | ggtccatccg | aagctggtga | cccagacctg | caccacttcg | 120 |
| ggaggttgtg | ttgaccgcca | aacattgctc | gtgacggatg | ccctctcgcg | tccgttccac | 180 |
| aaggttggag | atccttcggt | gccgtgcacg | ccgttgaaca | ccaccctctg | cccggacgcc | 240 |
| gccacttgtg | cggcaaactg | cgagctcgaa | ggggtggagt | atggtagcct | cggcgtgctt | 300 |
| accgccggcc | gagctgtcac | tctgcggcag | tacctcttcg | atggcgacgc | cttcacctct | 360 |
| gtcagcccgc | gcctctacct | gctggccgag | gacggcatga | actatgagct | gctcaagctg | 420 |
| aacggccaag | agctctccta | tgacgtcgac | gtgtcgcagc | tgggctgcgg | catgaatggc | 480 |
| gccttgtacc | tctccgagat | ggacgcctcg | ggtctagga | gcgacctgaa | cccagcaggt | 540 |
| gcccagtatg | gcacgggcta | ctgcgatgcg | cagtgcttta | atgtgtcgtt | atcaacgga | 600 |
| ctggtatgtg | tcgtggaat | gaacgtatc | cgtcatagcc | aagtcaaaca | tgaactaact | 660 |
| cttcacacat | cttcctccga | cagccgaatc | tcaacaactc | gggtgcctgc | tgcaacgaga | 720 |
| tggatatctg | ggaagcaaat | gccatggcta | ccgccatgac | gcctcatacc | tgcagcggcg | 780 |
| tgggctcctt | cttgtgctct | ggcgacgagt | gtggcaagac | cgacgccggc | gtatgcgacc | 840 |
| acgacggttg | cggcgtcaac | ccattccgcg | cgggcctcaa | agacttctac | ggccccggca | 900 |
| agaccgtgga | caccaccaaa | cccttcacgg | tggtgactca | gttttttgacc | gactctggca | 960 |
| atgcctctac | cggttcgggg | acgctcgccg | agatccgtcg | cctgtacgtc | caggacggca | 1020 |
| aggtcatcca | gaacgagccc | gtcccctcga | cacgaaccca | gctcgactct | acgtcgccca | 1080 |
| acgtgaacga | cgccagcggc | ggatccgtga | cgcaagcctt | ctgcaccgcc | gccaatgcct | 1140 |
| cgcagtacct | ccgcctgggg | ggcatggatg | gcatgggcgc | ctcgctggag | cgcggcatgg | 1200 |
| tactcgtctt | cagcatctgg | aactcggcgg | gcgacttcat | gaactggctg | acagcggcg | 1260 |
| aggccggccc | gtgcagcaac | acctccggcg | accggcccg | catcgtggcc | gagacgcccg | 1320 |
| aagtctccgt | caccttctcc | aacatccgct | ggggagatat | tgggtccacc | ttcaacggcg | 1380 |
| gcaaccctcc | cggcggaaac | cgtggcacca | ccaccacccg | ccgccagcc | actaccactg | 1440 |
| gaagctctcc | cggacctacc | cagtctcact | acggccagtg | cggcggtatt | ggctacagcg | 1500 |

-continued

| gccccacggt ctgcgccagc ggcacaactt gccaggtcct gaacccttac tactctcagt | 1560 |
| gcctgtaa | 1568 |

<210> SEQ ID NO 26
<211> LENGTH: 1395
<212> TYPE: DNA
<213> ORGANISM: Acremonium thermophilum

<400> SEQUENCE: 26

| atggcgcgcc agactcattc ctacggcatc ttggccgtcg cccttgtctt ctggcgccag | 60 |
| ctggctcacg ctcagaaccc agccgcgccc gaggtgcatc cgtcgctgcc cacctggaag | 120 |
| tgcaccacgg cgggcggttg cgtgcagcag aacacgtccg tcgtgctcga ctgggacgcg | 180 |
| cgcgccatcg tgccgtctgg cggcggcggc ggcggcggtg cgggtcctg caagacggcc | 240 |
| accggcggcg tcagtgccag cctctgtccc gacgaggcca cctgcgccaa gaactgcgtc | 300 |
| gtccagccca tcgccaacta cggagcac ggcgtgtcca ccgcgggcga cgccctgacc | 360 |
| ctgtaccact acgtgcgcat caacggccag ctgtcggccc agtcgccccg cgtctacctg | 420 |
| ctgggcccgg acggcgacta cgagatgctg cacctcctgg ccgcgagct cagcttcgac | 480 |
| gtcgacctgt ccacgctgcc ctgcggcgag aacggcgccc tctacctctc cgagatgagc | 540 |
| gccggcggcg gcgcaaccc cgacaacacg ggcggcgcga gctacggctc gggctactgc | 600 |
| gacgccagt gccccaccct ggcgtggcgc aacggcacca tcaacaccgg ccgccagggc | 660 |
| tactgctgcg acgagatgga catcctggag gccaactcgc aggccaacgc cttcaccccg | 720 |
| caccctgca ggaacggcaa ctgcgacaag agcggctgcg gctacaaccc ctacgccaag | 780 |
| ggcttccgca actactgggg ccccggtatg accgtcgaca cgtccaagcc cttcaccatc | 840 |
| accacccagt tcgtcgagag tggcgggtcc ctcagccaga tcgtgcgcag gtacgcccag | 900 |
| ggcgggcggc cgatccccag cgcggcgtcg ggcggcgacg tcatccaggc cagcgcctgc | 960 |
| ggcacgcgc agagcttcgg cgggctggcc gagatgggcg cggcgctgga ccgcggcatg | 1020 |
| gtcctcgtct tcagcatctg gaacgacccg gcccagaaca tgaactggct cgacagcggc | 1080 |
| accgcgggc cctgcagcag cgcggcgggc agtccggcca cgatccaggc gcagcatccg | 1140 |
| gatacgcacg ttgtcttctc gaacatccgc tggggcgaca ttggctcgac gacccagacg | 1200 |
| tcgggcggca accctcccgg cggaaaccgt ggcaccacca ccaccccgcc cccagccact | 1260 |
| accactggaa gctctcccgg acctacccag tctcactacg gccagtgcgg cggtattggc | 1320 |
| tacagcggcc ccacggtctg cgccagcggc acaacttgcc aggtcctgaa cccttactac | 1380 |
| tctcagtgcc tgtaa | 1395 |

<210> SEQ ID NO 27
<211> LENGTH: 495
<212> TYPE: PRT
<213> ORGANISM: Acremonium thermophilum

<400> SEQUENCE: 27

Met Ala Phe Arg Leu Ala Ala Ala Leu Pro Phe Leu Leu Leu Leu Ala
1               5                   10                  15

His Ala Gln Lys Ile Gly Thr Ala Val Pro Glu Val His Pro Lys Leu
            20                  25                  30

Val Thr Gln Thr Cys Thr Thr Ser Gly Gly Cys Val Asp Arg Gln Thr
        35                  40                  45

Leu Leu Val Thr Asp Ala Leu Ser Arg Pro Phe His Lys Val Gly Asp
    50                  55                  60

```
Pro Ser Val Pro Cys Thr Pro Leu Asn Thr Thr Leu Cys Pro Asp Ala
 65                  70                  75                  80

Ala Thr Cys Ala Ala Asn Cys Glu Leu Glu Gly Val Glu Tyr Gly Ser
             85                  90                  95

Leu Gly Val Leu Thr Ala Gly Arg Ala Val Thr Leu Arg Gln Tyr Leu
            100                 105                 110

Phe Asp Gly Asp Ala Phe Thr Ser Val Ser Pro Arg Leu Tyr Leu Leu
            115                 120                 125

Ala Glu Asp Gly Met Asn Tyr Glu Leu Leu Lys Leu Asn Gly Gln Glu
        130                 135                 140

Leu Ser Tyr Asp Val Asp Val Ser Gln Leu Gly Cys Gly Met Asn Gly
145                 150                 155                 160

Ala Leu Tyr Leu Ser Glu Met Asp Ala Ser Gly Ser Arg Ser Asp Leu
                165                 170                 175

Asn Pro Ala Gly Ala Gln Tyr Gly Thr Gly Tyr Cys Asp Ala Gln Cys
            180                 185                 190

Phe Asn Val Ser Phe Ile Asn Gly Leu Pro Asn Leu Asn Asn Ser Gly
            195                 200                 205

Ala Cys Cys Asn Glu Met Asp Ile Trp Glu Ala Asn Ala Met Ala Thr
        210                 215                 220

Ala Met Thr Pro His Thr Cys Ser Gly Val Gly Ser Phe Leu Cys Ser
225                 230                 235                 240

Gly Asp Glu Cys Gly Lys Thr Asp Ala Gly Val Cys Asp His Asp Gly
                245                 250                 255

Cys Gly Val Asn Pro Phe Arg Ala Gly Leu Lys Asp Phe Tyr Gly Pro
            260                 265                 270

Gly Lys Thr Val Asp Thr Thr Lys Pro Phe Thr Val Val Thr Gln Phe
            275                 280                 285

Leu Thr Asp Ser Gly Asn Ala Ser Thr Gly Ser Gly Thr Leu Ala Glu
        290                 295                 300

Ile Arg Arg Leu Tyr Val Gln Asp Gly Lys Val Ile Gln Asn Glu Pro
305                 310                 315                 320

Val Pro Ser Asn Thr Asn Gln Leu Asp Ser Thr Ser Pro Asn Val Asn
                325                 330                 335

Asp Ala Ser Gly Gly Ser Val Thr Gln Ala Phe Cys Thr Ala Ala Asn
            340                 345                 350

Ala Ser Gln Tyr Leu Arg Leu Gly Gly Met Asp Gly Met Gly Ala Ser
        355                 360                 365

Leu Glu Arg Gly Met Val Leu Val Phe Ser Ile Trp Asn Ser Ala Gly
        370                 375                 380

Asp Phe Met Asn Trp Leu Asp Ser Gly Glu Ala Gly Pro Cys Ser Asn
385                 390                 395                 400

Thr Ser Gly Asp Pro Ala Arg Ile Val Ala Glu Thr Pro Glu Val Ser
                405                 410                 415

Val Thr Phe Ser Asn Ile Arg Trp Gly Asp Ile Gly Ser Thr Phe Asn
            420                 425                 430

Gly Gly Asn Pro Pro Gly Gly Asn Arg Gly Thr Thr Thr Arg Arg
        435                 440                 445

Pro Ala Thr Thr Thr Gly Ser Ser Pro Gly Pro Thr Gln Ser His Tyr
            450                 455                 460
```

```
Gly Gln Cys Gly Gly Ile Gly Tyr Ser Gly Pro Thr Val Cys Ala Ser
465                 470                 475                 480

Gly Thr Thr Cys Gln Val Leu Asn Pro Tyr Tyr Ser Gln Cys Leu
                485                 490                 495

<210> SEQ ID NO 28
<211> LENGTH: 464
<212> TYPE: PRT
<213> ORGANISM: Acremonium thermophilum

<400> SEQUENCE: 28

Met Ala Arg Gln Thr His Ser Tyr Gly Ile Leu Ala Val Ala Leu Val
1               5                   10                  15

Phe Trp Arg Gln Leu Ala His Ala Gln Asn Pro Ala Ala Pro Glu Val
                20                  25                  30

His Pro Ser Leu Pro Thr Trp Lys Cys Thr Thr Ala Gly Gly Cys Val
            35                  40                  45

Gln Gln Asn Thr Ser Val Val Leu Asp Trp Asp Ala Arg Ala Ile Val
50                  55                  60

Pro Ser Gly Gly Gly Gly Gly Gly Gly Ser Cys Lys Thr Ala
65                  70                  75                  80

Thr Gly Gly Val Ser Ala Ser Leu Cys Pro Asp Glu Ala Thr Cys Ala
                85                  90                  95

Lys Asn Cys Val Val Gln Pro Ile Ala Asn Tyr Thr Glu His Gly Val
            100                 105                 110

Ser Thr Ala Gly Asp Ala Leu Thr Leu Tyr His Tyr Val Arg Ile Asn
        115                 120                 125

Gly Gln Leu Ser Ala Gln Ser Pro Arg Val Tyr Leu Leu Gly Pro Asp
130                 135                 140

Gly Asp Tyr Glu Met Leu His Leu Leu Gly Arg Glu Leu Ser Phe Asp
145                 150                 155                 160

Val Asp Leu Ser Thr Leu Pro Cys Gly Glu Asn Gly Ala Leu Tyr Leu
                165                 170                 175

Ser Glu Met Ser Ala Gly Gly Arg Asn Pro Asp Asn Thr Gly Gly
            180                 185                 190

Ala Ser Tyr Gly Ser Gly Tyr Cys Asp Ala Gln Cys Pro Thr Leu Ala
        195                 200                 205

Trp Arg Asn Gly Thr Ile Asn Thr Gly Arg Gln Gly Tyr Cys Cys Asp
210                 215                 220

Glu Met Asp Ile Leu Glu Ala Asn Ser Gln Ala Asn Ala Phe Thr Pro
225                 230                 235                 240

His Pro Cys Arg Asn Gly Asn Cys Asp Lys Ser Gly Cys Gly Tyr Asn
                245                 250                 255

Pro Tyr Ala Lys Gly Phe Arg Asn Tyr Trp Gly Pro Gly Met Thr Val
            260                 265                 270

Asp Thr Ser Lys Pro Phe Thr Ile Thr Thr Gln Phe Val Glu Ser Gly
        275                 280                 285

Gly Ser Leu Ser Gln Ile Val Arg Arg Tyr Ala Gln Gly Gly Arg Pro
290                 295                 300

Ile Pro Ser Ala Ala Ser Gly Gly Asp Val Ile Gln Ala Ser Ala Cys
305                 310                 315                 320

Gly Thr Ala Gln Ser Phe Gly Gly Leu Ala Glu Met Gly Ala Ala Leu
                325                 330                 335

Asp Arg Gly Met Val Leu Val Phe Ser Ile Trp Asn Asp Pro Ala Gln
            340                 345                 350
```

-continued

```
Asn Met Asn Trp Leu Asp Ser Gly Thr Ala Gly Pro Cys Ser Ser Ala
        355                 360                 365

Ala Gly Ser Pro Ala Thr Ile Gln Ala Gln His Pro Asp Thr His Val
    370                 375                 380

Val Phe Ser Asn Ile Arg Trp Gly Asp Ile Gly Ser Thr Thr Gln Thr
385                 390                 395                 400

Ser Gly Gly Asn Pro Pro Gly Gly Asn Arg Gly Thr Thr Thr Thr Arg
                405                 410                 415

Arg Pro Ala Thr Thr Thr Gly Ser Ser Pro Gly Pro Thr Gln Ser His
            420                 425                 430

Tyr Gly Gln Cys Gly Gly Ile Gly Tyr Ser Gly Pro Thr Val Cys Ala
        435                 440                 445

Ser Gly Thr Thr Cys Gln Val Leu Asn Pro Tyr Tyr Ser Gln Cys Leu
    450                 455                 460
```